United States Patent
Scott et al.

(10) Patent No.: US 11,890,353 B2
(45) Date of Patent: Feb. 6, 2024

(54) ANTI-POLYETHYLENE GLYCOL (PEG) ANTIBODY MOUSE MODEL FOR RIGOROUS ASSESSMENT OF PEG-BASED THERAPIES

(71) Applicant: NORTHWESTERN UNIVERSITY, Evanston, IL (US)

(72) Inventors: Evan A. Scott, Northfield, IL (US); Guillermo A. Ameer, Chicago, IL (US); Jacqueline A. Burke, Chicago, IL (US); Helena Freire Haddad, Evanston, IL (US)

(73) Assignee: Northwestern University, Evanston, IL (US)

( * ) Notice: Subject to any disclaimer, the term of this patent is extended or adjusted under 35 U.S.C. 154(b) by 491 days.

(21) Appl. No.: 17/071,653

(22) Filed: Oct. 15, 2020

(65) Prior Publication Data

US 2021/0106697 A1    Apr. 15, 2021

Related U.S. Application Data

(60) Provisional application No. 62/915,608, filed on Oct. 15, 2019.

(51) Int. Cl.
*A61K 49/00* (2006.01)
*A01K 67/027* (2006.01)

(52) U.S. Cl.
CPC ........ *A61K 49/0008* (2013.01); *A01K 67/027* (2013.01); *A01K 2207/10* (2013.01); *A01K 2227/105* (2013.01); *A01K 2267/03* (2013.01)

(58) Field of Classification Search
None
See application file for complete search history.

(56) References Cited

U.S. PATENT DOCUMENTS 9,334,331 B2 *   5/2016  Igawa ............... C07K 16/40
10,421,807 B2 *  9/2019  Gonzales ........... A61P 11/00

OTHER PUBLICATIONS

Al Qaraghuli et al. (2020, Nature Scientific Reports 10:13969).*
Edwards et al. (2003, JMB 334:103-118).*
Lloyd et al. (2009, Protein Engineering, Eng. Design & Selection 22(3): 159-168).*
Goel et al. (2004, J. Immunol. 173: 7358-7367).*
Khan et al. (2014, J. Immunol. 192: 5398-5405).*
Poosarla et al. (2017, Biotechn. Bioeng. 114(6): 1331-1342).*
Rabia, et al. (2018, Biochemical Engineering Journal 137:365-374).*
Justice et al., 2016, Disease, Models & Mechanisms 9:101-103.*
Yang et al. (2015, Wiley Interdiscip. Rev. Nanomed. Nanobiotechnol. 7(5):655-677).*

Aad, G. et al. Search for Magnetic Monopoles and Stable High-Electric-Charge Objects in 13 Tev Proton-Proton Collisions with the ATLAS Detector. Phys Rev Lett 124, 031802. 2020.
Abuchowski, A. et al, "Alteration of immunological properties of bovine serum albumin by covalent attachment of polyethylene glycol," J. Biol. Chem., vol. 252, No. 11, pp. 3578-3581, 1977.
Agrawal B. Heterologous Immunity: Role in Natural and Vaccine-Induced Resistance to Infections. Front Immunol. 2019;10:2631.
Allen S, et al. Facile assembly and loading of theranostic polymersomes via multi-impingement flash nanoprecipitation. J Control Release. 2017;262:91-103.
Allen SD, et al. Benchmarking Bicontinuous Nanospheres against Polymersomes for in Vivo Biodistribution and Dual Intracellular Delivery of Lipophilic and Water-Soluble Payloads. ACS Applied Materials & Interfaces. 2018;10 (40):33857-66.
Allen SD, et al. Celastrol-loaded PEG-b-PPS nanocarriers as an anti-inflammatory treatment for atherosclerosis. Biomaterials Science. 2019;7(2):657-68.
Allen SD, et al. Polymersomes scalably fabricated via flash nanoprecipitation are non-toxic in non-human primates and associate with leukocytes in the spleen and kidney following intravenous administration. Nano Research. 2018.
Allen SD, et al. Rapid, Scalable Assembly and Loading of Bioactive Proteins and Immunostimulants into Diverse Synthetic Nanocarriers Via Flash Nanoprecipitation. J Vis Exp. 2018(138).
Amylon M.D. et al., "Intensive high-dose asparaginase consolidation improves survival for pediatric patients with T cell acute lymphoblastic leukemia and advanced stage lymphoblastic lymphoma: a Pediatric Oncology Group study," Leukemia, vol. 13, No. 3, pp. 335-342, Mar. 1999.
Aragam B, et al. Learning large-scale Bayesian networks with the sparsebn package. Journal of Statistical Software. 2019.
Armstrong J.K. et al., "Antibody against poly(ethylene glycol) adversely affects PEG-asparaginase therapy in acute lymphoblastic leukemia patients," Cancer, vol. 110, No. 1, pp. 103-111, Jul. 2007.
Bailon P. et al, "Polyethylene glycol-conjugated pharmaceutical proteins," Pharm. Sci. Technol. Today, vol. 1, No. 8, pp. 352-356, Nov. 1998.
Ban Z, et al. Machine learning predicts the functional composition of the protein corona and the cellular recognition of nanoparticles. Proceedings of the National Academy of Sciences. 2020;117(19):10492-9.
Bandilla, K.K. et al, "Immunoglobulin classes of antibodies produced in the primary and secondary responses in man," Clin. Exp. Immunol., vol. 5, No. 6, pp. 627-641, Dec. 1969.
Barenholz, Y. "Doxil—the first FDA-approved nano-drug: lessons learned," J. Control. Release Off. J. Control. Release Soc., vol. 160, No. 2, pp. 117-134, Jun. 2012.

(Continued)

*Primary Examiner* — Elizabeth C. Kemmerer
(74) *Attorney, Agent, or Firm* — Quarles & Brady LLP

(57) ABSTRACT

The present invention provides methods of making an in vivo animal model for detecting anti-poly(ethylene glycol) (PEG) antibodies. The methods of the disclosure comprises administering subcutaneously to an animal model a composition comprising antibodies against poly(ethylene glycol) chains with a molecular weight of at least 550 Da to maintain an anti-PEG antibody level within the animal model. The in vivo animal model can be used for testing and screening drugs and other compositions for adverse reactions, bioavailability, and immunogenicity prior to administration to a human subject.

19 Claims, 6 Drawing Sheets

(56) References Cited

OTHER PUBLICATIONS

Barnett K, et al. Epidemiology of multimorbidity and implications for health care, research, and medical education: a cross-sectional study. The Lancet. 2012;380(9836):37-43.
Bayer. "Doxil Package Insert." Baxter Healthcare Corporation, Aug. 2019, [Online]. Available: doxil.com.
Bobbala S, et al. Employing bicontinuous-to-micellar transitions in nanostructure morphology for on-demand photo-oxidation responsive cytosolic delivery and off-on cytotoxicity. Nanoscale. 2020; 12(9):5332-40.
Bobbala S, et al. Flash nanoprecipitation permits versatile assembly and loading of polymeric bicontinuous cubic nanospheres. Nanoscale. 2018;10(11):5078-88.
Boeckler et al., "Design of highly immunogenic liposomal constructs combining structurally independent B cell and T helper cell peptide epitopes," Eur. J. Immunol., vol. 29, No. 7, pp. 2297-2308, 1999.
Braun R, et al. Genetically Engineered Gold-Binding Polypeptides: Structure Prediction and Molecular Dynamics. Journal of Biomaterials Science. 2002;13:747-58.
Braun R, et al. Identifying Differential Correlation in Gene/Pathway Combinations. BMC Bioinformatics. 2008;9:488.
Braun R, et al. Molecular dynamics simulations of micelle formation around dimeric Glycophorin-A transmembrane helices. Biophysical Journal. 2004;87:754-63.
Braun R, et al. Network Methods for Pathway Analysis of Gene Expression Data. arXiv preprint arXiv:14111993. 2014.
Braun R, et al. Partition Decoupling for Multi-gene Analysis of Gene Expression Profiling Data. BMC Bioinformatics. 2011;12(497).
Braun R, et al. Pathways of Distinction Analysis: a new technique for multi-SNP analysis of GWAS data. PLoS Genetics. 2011;7(6):e1002101.
Braun R, et al. Reply to Laing et al.: Accurate prediction of circadian time across platforms. Proceedings of the National Academy of Sciences. 2019;116(12):5206-8.
Braun R, et al. Universal method for robust detection of circadian state from gene expression. Proceedings of the National Academy of Sciences. 2018;115(39):E9247-E56.
Braun R. Systems analysis of high-throughput data. Advances in Experimental Medicine and Biology. 2014;844:153.
Cai P, et al. Combinatorial Nano-Bio Interfaces. ACS Nano. 2018;12(6):5078-84.
Cerritelli S, et al. PEG-SS-PPS: reduction-sensitive disulfide block copolymer vesicles for intracellular drug delivery. Biomacromolecules. 2007;8(6):1966-72.
Chanan-Khan et al., "Complement activation following first exposure to pegylated liposomal doxorubicin (Doxil): possible role in hypersensitivity reactions," Ann. Oncol., vol. 14, No. 9, pp. 1430-1437, Sep. 2003.
Cohen J, et al. Imaging the migration pathways for O2, CO, NO, and Xe inside myoglobin. Biophysical Journal. 2006;91:1844-57.
Dams ETM et al., "Accelerated Blood Clearance and Altered Biodistribution of Repeated Injections of Sterically Stabilized Liposomes," J. Pharmacol. Exp. Ther., vol. 292, No. 3, pp. 1071-1079, Mar. 2000.
Deen, WM et al, "Structural determinants of glomerular permeability," Am. J. Physiol.-Ren. Physiol., vol. 281, No. 4, pp. F579-F596, Oct. 2001.
Delgado, C. et al, "The uses and properties of PEG-linked proteins," Crit. Rev. Ther. Drug Carrier Syst., vol. 9, No. 3-4, pp. 249-304, 1992.
Demissie A, et al. Healthy individuals that control a latent infection with *Mycobacterium tuberculosis* express high levels of Th1 cytokines and the IL-4 antagonist IL-4delta2. J Immunol. 2004;172(11):6938-43.
Dimasi, J. A., et al. The cost of drug development. N Engl J Med 372, 1972 (2015).
Dowling DJ, et al. Toll-like receptor 8 agonist nanoparticles mimic immunomodulating effects of the live BCG vaccine and enhance neonatal innate and adaptive immune responses. J Allergy Clin Immunol. 2017.
Du F, et al. Immunotheranostic Polymersomes Modularly Assembled from Tetrablock and Diblock Copolymers with Oxidation-Responsive Fluorescence. Cellular and Molecular Bioengineering. 2017; 10(5):357-70.
Du F, et al. Sequential intracellular release of water-soluble cargos from Shell-crosslinked polymersomes. J Control Release. 2018,282:90-100.
Frey M, et al. Mapping the supramolecular assembly space of poly(sarcosine)-b-poly(propylene sulfide) using a combinatorial copolymer library. Chem Commun (Camb). 2020;56(49):6644-7.
Fruijtier-Polloth, C. Safety assessment on polyethylene glycols (PEGs) and their derivatives as used in cosmetic products. Toxicology 214, 1-38 (2005).
Ganson N.J. et al., "Control of hyperuricemia in subjects with refractory gout, and induction of antibody against poly (ethylene glycol) (PEG), in a phase I trial of subcutaneous PEGylated urate oxidase," Arthritis Res. Ther., vol. 8, No. 1, p. R12, 2006.
Ganson N.J. et al., "Pre-existing anti-polyethylene glycol antibody linked to first-exposure allergic reactions to begnivacogin, a PEGylated RNA aptamer," J. Allergy Clin. Immunol., vol. 137, No. 5, pp. 1610-1613.e7, May 2016.
Gullingsrud J, et al. Reconstructing Potentials of Mean Force Through Time Series Analysis of Steered Molecular Dynamics Simulations. Journal of Computational Physics. 1999; 151:190-211.
Hanzelmann S, et al. GSVA: gene set variation analysis for microarray and RNA-seq data. BMC Bioinformatics. 2013;14:7.
Harris J.M. et al, "Effect of pegylation on pharmaceuticals," Nat. Rev. Drug Discov., vol. 2, No. 3, Art. No. 3, Mar. 2003.
Harris J.M. et al, "Pegylation," Clin. Pharmacokinet., vol. 40, No. 7, pp. 539-551, Jul. 2001.
Hay, M., et al. Clinical development success rates for investigational drugs. Nat Biotechnol 32, 40-51 (2014).
Henriksen LT et al., "PEG-asparaginase allergy in children with acute lymphoblastic leukemia in the NOPHO ALL2008 protocol," Pediatr. Blood Cancer, vol. 62, No. 3, pp. 427-433, 2015.
Hershfield, M. S. et al, "Induced and pre-existing anti-polyethylene glycol antibody in a trial of every 3-week dosing of pegloticase for refractory gout, including in organ transplant recipients," Arthritis Res. Ther., vol. 16, No. 2, p. R63, Mar. 2014.
Hershman DL, et al. Doxorubicin, cardiac risk factors, and cardiac toxicity in elderly patients with diffuse B-cell non-Hodgkin's lymphoma. J Clin Oncol. 2008;26(19):3159-65.
Hoang Thi, T. T. et al. The Importance of Poly(ethylene glycol) Alternatives for Overcoming PEG Immunogenicity in Drug Delivery and Bioconjugation. Polymers (Basel) 12, (2020).
Hsieh, M. J. et al. Comparative efficacy and tolerability of beclomethasone/formoterol and fluticasone/salmeterol fixed combination in Taiwanese asthmatic patients. J Formos Med Assoc 117, 1078-1085, (2018).
Hsieh, Y. C. et al. Pre-existing anti-polyethylene glycol antibody reduces the therapeutic efficacy and pharmacokinetics of PEGylated liposomes. Theranostics 8, 3164-3175, (2018).
Ishida, T. et al, "Accelerated clearance of a second injection of PEGylated liposomes in mice," Int. J. Pharm., vol. 255, No. 1, pp. 167-174, Apr. 2003.
Jang, H.-J. et al, "Safety Evaluation of Polyethylene Glycol (PEG) Compounds for Cosmetic Use," Toxicol. Res., vol. 31, No. 2, pp. 105-136, Jun. 2015.
Judge, A. et al, "Hypersensitivity and Loss of Disease Site Targeting Caused by Antibody Responses to PEGylated Liposomes," Mol. Ther., vol. 13, No. 2, pp. 328-337, Feb. 2006.
Karabin NB, et al. Sustained micellar delivery via inducible transitions in nanostructure morphology. Nat Commun. 2018;9(1):624.
Karabin NB, et al. The Combination of Morphology and Surface Chemistry Defines the Biological Identity of Nanocarriers in Human Blood. bioRxiv. 2020.
Karl S. et al, "Pro and contra of specific hyposensitization," Eur. J. Dermatol. EJD, vol. 9, No. 4, pp. 325-331, Jun. 1999.
Kloos, R. et al, "Acute lymphoblastic leukaemia patients treated with PEGasparaginase develop antibodies to PEG and the succinate linker," Br. J. Haematol., vol. 189, No. 3, pp. 442-451, 2020.

(56) References Cited

OTHER PUBLICATIONS

Le TC, et al. Discovery and Optimization of Materials Using Evolutionary Approaches. Chem Rev. 2016;116 (10):6107-32.
Li, W.M. et al, "Enhanced immune response to T-independent antigen by using CpG oligodeoxynucleotides encapsulated in liposomes," Vaccine, vol. 20, No. 1-2, pp. 148-157, Oct. 2001.
Liu R, et al. Prediction of nanoparticles-cell association based on corona proteins and physicochemical properties. Nanoscale. 2015;7(21):9664-75.
Longmire, M. et al, "Clearance properties of nano-sized particles and molecules as imaging agents: considerations and caveats," Nanomed., vol. 3, No. 5, pp. 703-717, Sep. 2008.
Love MI, et al. Moderated estimation of fold change and dispersion for RNA-seq data with DESeq2. Genome Biol. 2014;15(12):550.
Marrink SJ, et al. Computational modeling of realistic cell membranes. Chemical reviews. 2019;119(9):6184-226.
Marrink SJ, et al. The MARTINI force field: coarse grained model for biomolecular simulations. The journal of physical chemistry B. 2007;111(27):7812-24.
Monticelli L, et al. The MARTINI coarse-grained force field: extension to proteins. Journal of chemical theory and computation. 2008;4(5):819-34.
Muller H.J. et al, "Use of L-asparaginase in childhood ALL," Crit. Rev. Oncol. Hematol., vol. 28, No. 2, pp. 97-113, Aug. 1998.
Nagaraj R, et al. High Density Display of an Anti-Angiogenic Peptide on Micelle Surfaces Enhances Their Inhibition of $\alpha v \beta 3$ Integrin-Mediated Neovascularization In Vitro. Nanomaterials (Basel). 2020; 10(3).
Napoli A, et al. Lyotropic Behavior in Water of Amphiphilic ABA Triblock Copolymers Based on Poly(propylene sulfide) and Poly(ethylene glycol). Langmuir. 2002;18(22):8324-9.
Neun, B. et al, "Understanding the Role of Anti-PEG Antibodies in the Complement Activation by Doxil in Vitro," Molecules, vol. 23, No. 7, p. 1700, Jul. 2018.
Nguyen P, et al. Semi-supervised network inference using simulated gene expression dynamics. Bioinformatics. 2017;34(7):1148-56.
Nguyen P, et al. Time-lagged Ordered Lasso for network inference. BMC Bioinformatics. 2018;19(1):545.
Nikitin MP, et al. Enhancement of the blood-circulation time and performance of nanomedicines via the forced clearance of erythrocytes. Nat Biomed Eng. 2020;4(7):717-31.
O'Hagan DT et al, "Microparticles as vaccine adjuvants and delivery systems," Expert Rev. Vaccines, vol. 2, No. 2, pp. 269-283, Apr. 2003.
Ozmen, L. et al. Inhibition of thrombin abrogates the instant blood-mediated inflammatory reaction triggered by isolated human islets: possible application of the thrombin inhibitor melagatran in clinical islet transplantation. Diabetes 51, 1779-1784. 2002.
Pang, S. N. J. "Final report on the safety assessment of polyethylene glycols (PEGs)-6,-8,-32,-75,-150,-14M,-20M." Journal of the American College of Toxicology 12.5 (1993): 429-457.
Park T, et al. The bayesian lasso. Journal of the American Statistical Association. 2008;103(482):681-6.
Phillips JC, et al. Scalable Molecular Dynamics with NAMD. Journal of Computational Chemistry. 2005;26:1781-802.
Poma AB, et al. Combining the MARTINI and structure-based coarse-grained approaches for the molecular dynamics studies of conformational transitions in proteins. Journal of Chemical Theory and Computation. 2017;13(3):1366-74.
Povsic T.J. et al., "A Phase 2, randomized, partially blinded, active-controlled study assessing the efficacy and safety of variable anticoagulation reversal using the REG1 system in patients with acute coronary syndromes: results of the RADAR trial," Eur. Heart J., vol. 34, No. 31, pp. 2481-2489, Aug. 2013.
Raghupathi W, et al. An Empirical Study of Chronic Diseases in the United States: A Visual Analytics Approach. Int J Environ Res Public Health. 2018;15(3).
Ramos-De-La-Peña A.M. et al, "Progress and Challenges in PEGylated Proteins Downstream Processing: A Review of the Last 8 Years," Int. J. Pept. Res. Ther., vol. 26, No. 1, pp. 333-348, Mar. 2020.

Richter A.W. et al, "Antibodies against Polyethylene Glycol Produced in Animals by Immunization with Monomethoxy Polyethylene Glycol Modified Proteins," Int. Arch. Allergy Immunol., vol. 70, No. 2, pp. 124-131, 1983.
Richter A.W. et al, "Polyethylene Glycol Reactive Antibodies in Man: Titer Distribution in Allergic Patients Treated with Monomethoxy Polyethylene Glycol Modified Allergens or Placebo, and in Healthy Blood Donors," Int. Arch. Allergy Immunol., vol. 74, No. 1, pp. 36-39, 1984.
Ridker PM, et al. Interleukin-1beta inhibition and the prevention of recurrent cardiovascular events: rationale and design of the Canakinumab Anti-inflammatory Thrombosis Outcomes Study (CANTOS). Am Heart J. 2011;162(4):597-605.
Schellekens, H. et al, "The Immunogenicity of Polyethylene Glycol: Facts and Fiction," Pharm. Res., vol. 30, No. 7, pp. 1729-1734, Jul. 2013.
Scott EA, et al. Dendritic cell activation and T cell priming with adjuvant- and antigen-loaded oxidation-sensitive polymersomes. Biomaterials. 2012;33(26):6211-9.
Scott EA, et al. Mass spectrometric mapping of fibrinogen conformations at poly(ethylene terephthalate) interfaces. Biomaterials. 2007;28(27):3904-17.
Scott EA, et al. Overcoming Immune Dysregulation with Immunoengineered Nanobiomaterials. Annu Rev Biomed Eng. 2017;19:57-84.
Scott EA. Immune Theranostics. In: National Academy of Engineering. Frontiers of Engineering: Reports on Leading-Edge Engineering from the 2018 Symposium. Washington (DC): National Academies Press (US); 2019.
Semple, S.C. et al, "Immunogenicity and Rapid Blood Clearance of Liposomes Containing Polyethylene Glycol-Lipid Conjugates and Nucleic Acid," J. Pharmacol. Exp. Ther., vol. 312, No. 3, pp. 1020-1026, Mar. 2005.
Shah SD, et al. GeneSurrounder: network-based identification of disease genes in expression data. BMC Bioinformatics. 2019,20:229.
Shang S, et al. Induction of *Mycobacterium tuberculosis* Lipid-Specific T Cell Responses by Pulmonary Delivery of Mycolic Acid-Loaded Polymeric Micellar Nanocarriers. Front Immunol. 2018;9:2709.
Silva D, et al. A whole blood assay as a simple, broad assessment of cytokines and chemokines to evaluate human immune responses to *Mycobacterium tuberculosis* antigens. Acta Trop. 2013;127(2):75-81.
Silverman LB et al., "Improved outcome for children with acute lymphoblastic leukemia: results of Dana-Farber Consortium Protocol 91-01," Blood, vol. 97, No. 5, pp. 1211-1218, Mar. 2001.
Soni D, et al. The Sixth Revolution in Pediatric Vaccinology: Immunoengineering and Delivery Systems. Pediatric Research. (2020): 1-9.
Sroda, K. et al, "Repeated injections of PEG-PE liposomes generate anti-PEG antibodies," Cell. Mol. Biol. Lett., vol. 10, No. 1, pp. 37-47, 2005.
Stack T, et al. Co-administration of macropinocytosis inhibitory nanoparticles (MiNP) for enhanced nanoparticle circulation time and target tissue accumulation following subcutaneous injection. bioRxiv. 2020:2020.08.26.267054.
Stack T, et al. Modulation of Schlemm's canal endothelial cell stiffness via latrunculin loaded block copolymer micelles. J Biomed Mater Res A. 2018;106(7):1771-9.
Stack T, et al. Targeted Delivery of Cell Softening Micelles to Schlemm's Canal Endothelial Cells for Treatment of Glaucoma. Small. 2020.
Stano A, et al. Tunable T cell immunity towards a protein antigen using polymersomes vs. solid-core nanoparticles. Biomaterials. 2013;34(17):4339-46.
Suykens JA, et al. Least squares support vector machine classifiers. Neural processing letters. 1999;9(3):293-300.
Swierczewska, M. et al, "What is the future of PEGylated therapies?," Expert Opin. Emerg. Drugs, vol. 20, No. 4, pp. 531-536, 2015.
Swirski FK, et al. Leukocyte Behavior in Atherosclerosis, Myocardial Infarction, and Heart Failure. Science. 2013;339(6116):161-6.

(56) References Cited

OTHER PUBLICATIONS

Szebeni J., "Complement activation-related pseudoallergy: A new class of drug-induced acute immune toxicity," Toxicology, vol. 216, No. 2, pp. 106-121, Dec. 2005.

Szebeni J., "The Interaction of Liposomes with the Complement System," Crit. Rev. Ther. Drug Carr. Syst., vol. 15, No. 1, 1998.

Tibshirani R et al. An ordered lasso and sparse time-lagged regression. Technometrics. 2016;58(4):415-23.

Tong W.H. et al., "A prospective study on drug monitoring of PEGasparaginase and Erwinia asparaginase and asparaginase antibodies in pediatric acute lymphoblastic leukemia," Blood, vol. 123, No. 13, pp. 2026-2033, Mar. 2014.

Torrice M. Does Nanomedicine Have a Delivery Problem? ACS Cent Sci. 2016;2(7):434-7.

Van Der Sluis I.M. et al., "Efficacy and safety of recombinant E. coli asparaginase in children with previously untreated acute lymphoblastic leukemia: A randomized multicenter study of the Dutch Childhood Oncology Group," Pediatr. Blood Cancer, vol. 65, No. 8, p. e27083, 2018.

Vandamme, T. F. Use of rodents as models of human diseases. J Pharm Bioallied Sci 6, 2-9. 2014.

Vasdekis AE, et al. Precision intracellular delivery based on optofluidic polymersome rupture. ACS Nano. 2012;6(9):7850-7.

Veronese, F. M et al. PEGylation, successful approach to drug delivery. Drug Discov Today 10, 1451-1458. 2005.

Vincent MP, et al. Surface chemistry-mediated modulation of adsorbed albumin folding state specifies nanocarrier clearance by distinct macrophage subsets. bioRxiv. 2020:2020.04.24.060772.

Von Rueden L, et al. Informed Machine Learning—A Taxonomy and Survey of Integrating Knowledge into Learning Systems. arXiv preprint arXiv:190312394. 2019.

Wilhelm S, et al. Analysis of nanoparticle delivery to tumours. Nat Rev Mater. 2016;1(5):16014.

Wilk G, et al. Integrative analysis reveals disrupted pathways regulated by microRNAs in cancer. Nucleic Acids Research. 2017;46(3):1089-101.

Wilk G, et al. regQTLs: Single nucleotide polymorphisms that modulate microRNA regulation of gene expression in tumors. PLoS Genetics. 2018;14(12):e1007837.

Yamankurt G, et al. Exploration of the nanomedicine-design space with high-throughput screening and machine learning. Nature biomedical engineering. 2019;3(4):318-27.

Yang Q. et al., "Analysis of Pre-existing IgG and IgM Antibodies against Polyethylene Glycol (PEG) in the General Population," Anal. Chem., vol. 88, No. 23, pp. 11804-11812, Dec. 2016.

Yesylevskyy SO, et al. Polarizable water model for the coarse-grained MARTINI force field. PLoS Comput Biol. 2010;6(6):e1000810.

Yi S, et al. An Injectable Hydrogel Platform for Sustained Delivery of Anti-inflammatory Nanocarriers and Induction of Regulatory T Cells in Atherosclerosis. Frontiers in Bioengineering and Biotechnology. 2020;8(542).

Yi S, et al. Surface Engineered Polymersomes for Enhanced Modulation of Dendritic Cells During Cardiovascular Immunotherapy. Advanced Functional Materials. 2019;29(42):1904399.

Yi S, et al. Tailoring Nanostructure Morphology for Enhanced Targeting of Dendritic Cells in Atherosclerosis. ACS Nano. 2016;10(12):11290-303.

Zhao Y. et al., "Repeated injection of PEGylated solid lipid nanoparticles induces accelerated blood clearance in mice and beagles," Int. J. Nanomedicine, vol. 7, pp. 2891-2900, 2012.

Scott EA. Immune Theranostics. The Bridge. vol. 48 Issue 4. p 34-39. Dec. 14, 2018.

Scott EA. Immune Theranostics. Presentation at 2018 US Frontiers of Engineering Symposium. Sep. 7, 2018. 24 pages.

* cited by examiner

ANTI-POLYETHYLENE GLYCOL (PEG) ANTIBODY MOUSE MODEL FOR RIGOROUS ASSESSMENT OF PEG-BASED THERAPIES

CROSS-REFERENCE TO RELATED APPLICATIONS

This application claims priority to U.S. Provisional Application No. 62/915,608, filed Oct. 15, 2019, the contents of which are incorporated by reference in its entirety.

STATEMENT REGARDING FEDERALLY SPONSORED RESEARCH

N/A

BACKGROUND OF THE INVENTION

Poly(ethylene glycol) (PEG) is a nontoxic, hydrophilic polymer that can be covalently attached to the surface of a protein, drug, tissue, or material, through a technique called PEGylation. PEGylation improves solubility, circulation time, and reduces immunogenicity of therapeutic molecules. Currently, there are 21 PEGylated drugs approved by the Food and Drug Administration (FDA), and more in the developmental stage. In addition to the polymer's applications in the clinic, PEG is widely used as a solvent and emulsifying agent in the formulation of cosmetics, cleaning, and personal care products.

During the drug development process, PEG containing drugs are assessed using animal models that are shielded from the PEG exposure common to daily human life. When novel drugs reach human trials, unexpected results, including inefficacy and adverse reactions, have occurred due to the presence of αPEG Abs in human blood. A 2013 Phase 2b clinical trial of Pegnivocagin, a PEGylated RNA aptamer for the inhibition of coagulation factor Ixa, patients with pre-existing αPEG Abs developed anaphylactic and skin reactions, resulting in the termination of the trial. [15,16]

Failure of drugs in human clinical trials pose a great financial and health burden on society. Bringing a drug from development to the market is estimated to exceed $2.5 billion[17]. Risk of failure in clinical trials is high—averaging 95%[18]. Most critically, dire health outcomes may result from adverse drug effects[17,19]. Eliminating drug candidates that will fail in clinical trials before economic effect and human health are put at risk is vital for society[17,19].

Thus, there is a great need for an animal model to recapitulate concentrations of αPEG Abs found in human blood to assess novel therapeutics prior to human trial. A variety of approaches have been described in literature to create αPEG Abs animal models. Mouse models are ideal due to their commonality in research, low cost and small size[20]. Passive transfer (PT) models consist of exposing animals to highly characterized, commercially available monoclonal antibodies. Previous PT models utilize the intravenous (IV) route of administration[21]. However, none have successfully captured the state of pre-existing αPEG Abs known to be present in the general population at relevant concentrations.

The present disclosure solves the need in the art by providing a method for developing an animal model that successfully captures the state of pre-existing αPEG Abs at relevant concentrations.

SUMMARY OF THE INVENTION

The present invention is related to an in vivo animal model that can be used for monitoring and detecting anti-poly(ethylene-glycol) (PEG) antibodies and use in screening drugs and therapeutics.

In one aspect, the disclosure provides a method of making an in vivo model for detecting and monitoring anti-poly (ethylene glycol) (PEG) antibodies and subsequent immune responses, the method comprising: (a) administering subcutaneously to an animal model a composition comprising antibodies against poly(ethylene glycol) chains with a molecular weight of at least 550 Da; and (b) detecting anti-PEG antibodies within the animal model at a level of at least 44 ng/ml, wherein the in vivo animal model can be used to test compositions for the ability to be recognized by anti-PEG.

In another aspect, the disclosure provides a method of making an in vivo model for detecting, monitoring anti-poly (ethylene glycol) (PEG) antibodies, the method comprising: (a) administering subcutaneously to an animal model a composition comprising antibodies against one or more poly(ethylene glycol) chains with a molecular weight with a molecular weight of at least 550 Da; (b) administering one or more booster injections subcutaneously at least 14 days after step (a); and (c) detecting anti-PEG antibodies within the animal model at a level of at least 44 ng/ml, wherein the in vivo animal model can be used to test compositions for their reactivity to anti-PEG antibodies in vivo.

In a further aspect, the disclosure provides a method of testing an adjuvant/stimulatory molecule in the in vivo animal model described herein, the method comprising: (a) administering the adjuvant/stimulatory molecule to the in vivo animal model; (b) detecting changes in effective dose, pharmacokinetics, biodistribution, immunogenicity or a combination thereof of the adjuvant/stimulatory molecule in the animal model compared to the effective dose, pharmacokinetics and/or biodistribution, and immunogenicity of the adjuvant/stimulatory molecule in a control animal model without anti-PEG antibodies.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
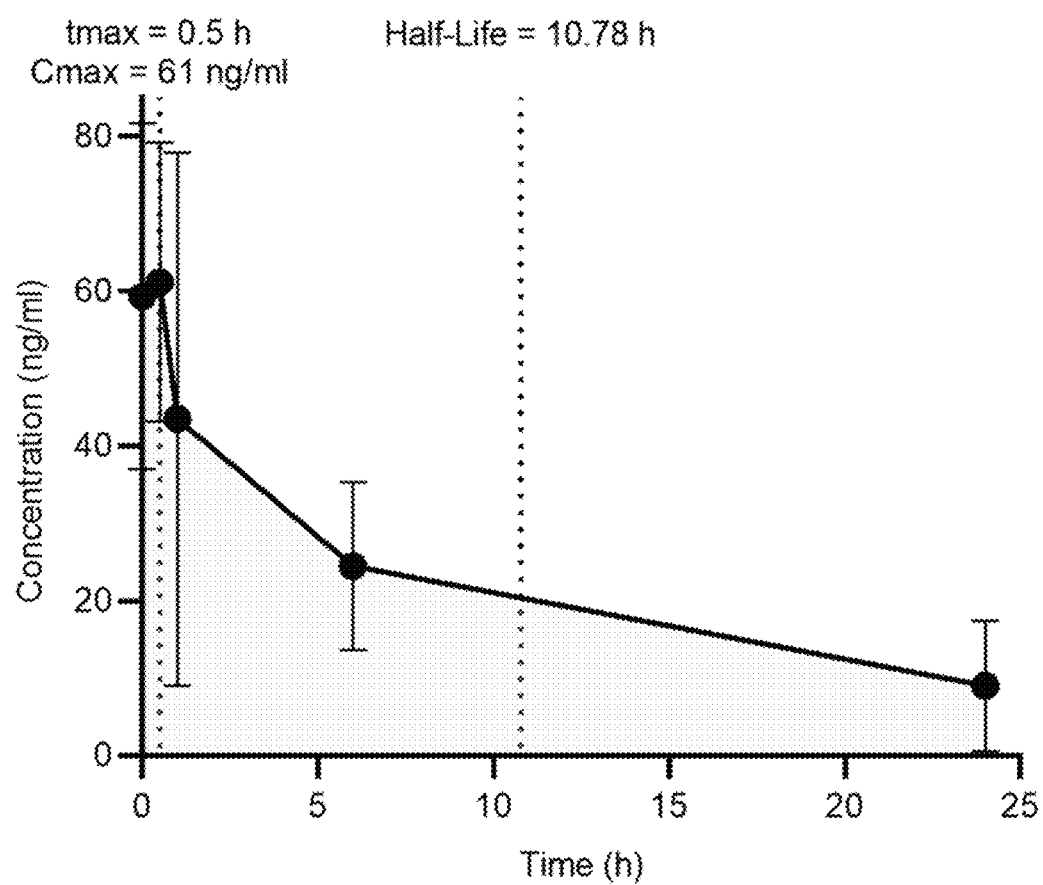
FIG. 1 is a graph showing the blood concentration of anti-PEG IgG antibodies in mice injected intravenously with anti-PEG antibodies at a dose of 7.5 μg/kg, assessed via ELISA, as a function of time. (n=5).

The present invention has been described in terms of one or more preferred embodiments, and it should be appreciated that many equivalents, alternatives, variations, and modifications, aside from those expressly stated, are possible and within the scope of the invention.

The present disclosure describes methods of making in vivo models for detecting anti-poly(ethylene glycol) (PEG) antibodies (αPEG Abs), that can then be used for screening for interactions with adjuvants, drugs and compositions containing PEG that, when administered, if interact with anti-PEG antibodies, may alter their effective dose, pharmocokinetics, biodistribution, immunogenicity or potential adverse reactions in vivo. The present disclosure provides methods of use of the in vivo models for screening drugs, PEG-based therapeutics, PEG-based nanoparticles/nanocarrier platforms, PEGylated devices and PEG-containing products, including personal care products, for adverse reactions or altered activities as described more below. Further, the in vivo model can be used to understand how variations in anti-PEG antibody concentrations within various populations impact alterations in effective dose, pharmacokinetics and/or biodistribution, immunogenicity, or potential adverse reactions to drugs and compositions. The presence of high concentrations of αPEG Abs in blood due to exposure from personal care products and everyday items can result in decreased treatment efficacy and allergic reactions to PEGylated drugs that may be useful for treating a myriad of disorders and diseases.

In some embodiments, the method of the present disclosure comprises (a) administering subcutaneously to an animal model a composition comprising antibodies against poly(ethylene glycol) chains with a molecular weight of at least 550 Da.

In some embodiments, the time between the initial subcutaneous injection and the time in which experimentation can begin is from 5 days to 50 days. In some embodiments, the time between initial subcutaneous injection and experimentation is from 10 days to 45 days. In some embodiments, the time between initial subcutaneous injection and experimentation is from 25 days to 40 days. One skilled in the art would understand that the time between initial subcutaneous injection and experimental period is dependent on various factors. For example, the time between the initial subcutaneous injection and experimental period is dependent on three factors, including initial subcutaneous dose, desired target anti-PEG antibody concentration and the acceptable range of anti-PEG antibody concentration around that target. For example, in an embodiment where a single 100 µg/kg anti-PEG antibody dose is injected, where the target anti-PEG antibody concentration is 52 ng/ml and the confidence interval is between 44 and 62 ng/ml, the animal model can be used for experimentation about 38 days after the initial subcutaneous injection. In another embodiment, where a single 50 µg/kg anti-PEG antibody dose is injected, where the target anti-PEG antibody concentration is 52 ng/ml and the confidence interval is between 44 and 62 ng/ml, the animal model can be used for experimentation about 28 days after the initial subcutaneous injection.

Figure 5:
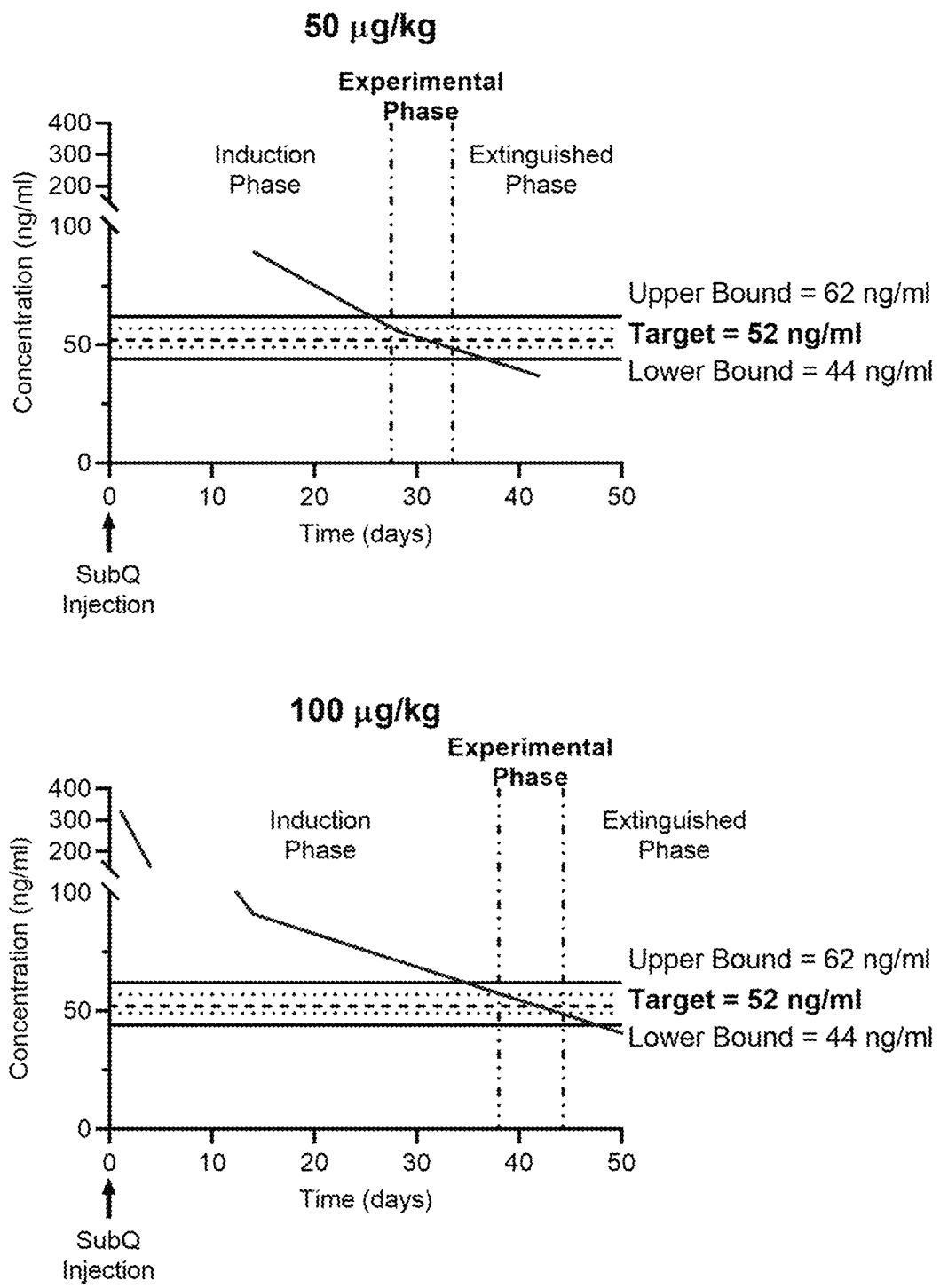
FIG. 5 are graphs showing the concentration of anti-PEG IgG antibodies in mice injected subcutaneously with anti-PEG antibodies at doses of 50 μg/kg (top) or 100 μg/kg (bottom), assessed via ELISA, as a function of time. These graphs are examples of the Single Injection Model. The target concentration is defined as 52 ng/ml. With an upper bound of 62 ng/ml and a lower bound of 44 ng/ml. Top: With a single dose of 50 μg/kg, the induction phase occurs from day 0 to 28. The experimental phase starts when the concentration reaches 10% of the target less than the upper bound (62 ng/ml-10% (52 ng/ml)=62 ng/ml-5 ng/ml=57 ng/ml). This occurs at day 28. The experimental phase ends when the concentration reaches 10% of the target greater than the lower bound (44 ng/ml+10% (52 ng/ml)=44 ng/ml+5 ng/ml=49 ng/ml). This occurs at day 34. Thus, the experimental phase is maintained for approximately 6 days. The extinguished phase occurs after day 34. Bottom: With a single dose of 100 μg/kg, the induction phase occurs from day 0 to 38. The experimental phase starts when the concentration reaches 10% of the target less than the upper bound (62 ng/ml-10% (52 ng/ml)=62 ng/ml-5 ng/ml=57 ng/ml). This occurs at day 38. The experimental phase ends when the concentration reaches 10% of the target greater than the lower bound (44 ng/ml+10% (52 ng/ml)=44 ng/ml+5 ng/ml=49 ng/ml). This occurs at day 44. Thus, the experimental phase is maintained for approximately 6 days. The extinguished phase occurs after day 44.

By "administering" when referring to the making of the animal model, the term refers to introducing the anti-poly(ethylene glycol) (PEG) antibodies or compositions comprising said anti-PEG antibodies into the animal model subcutaneously. Without wishing to be bound to theory, subcutaneous injection extends the half-life of αPEG Abs and enhances ease of model maintenance, in terms of both improved ease of injection method and reduced frequency of injection. It was unexpectedly found that the administration of the passively transferred antibodies subcutaneously as opposed to intravenously (e.g., tail vein), allows for the ability to provide an animal model that retains a level of anti-PEG antibodies within the animal in at a suitable amount that can be sued for screening other drugs or compositions (e.g., having anti-PEG antibodies at a level of at least 44 ng/ml, preferably from 44 ng/ml to 62 ng/ml). (FIG. 5). Depending on the model parameters the skilled artisan wishes to use/accomplish, which may include anti-PEG antibody dose, target anti-PEG antibody concentration, range of anti-PEG antibody concentration, and type of model (single injection or multiple injection), the amount of time that the model can be maintained can be determined. For example, in embodiments encompassing the single injection model, the model can be maintained for 2 to 30 days. For example, in a particular embodiment where a single 100 µg/kg anti-PEG antibody dose is injected, with a target anti-PEG antibody concentration of 52 ng/ml and a confidence interval between 44 and 62 ng/ml, the model can be used for experimentation for 6 days during a period of 38 days to 44 days after an initial subcutaneous injection (FIG. 5). In another embodiment, where a single injection dose of 50 µg/kg is injected, with a target anti-PEG antibody concentration of 52 ng/ml and a confidence interval between 44 and 62 ng/ml, the model can be also be used for an experimental phase of 6 days occurring from 28 days to 34 days after initial injection (FIG. 5). Other suitable timings and ranges of use can be determined by one skilled in the art.

In embodiments encompassing the multiple injection model, the antibody concentration can be maintained for the lifetime of the animal as long as the booster injection occur.

The term "administering" when related to the testing of a PEG-containing drugs, nanocarriers, and compositions in the animal models, may use any suitable means for delivering to the animal. Examples include, but are not limited to oral, buccal, sublingual, pulmonary, transdermal, transmucosal, as well as subcutaneous, intravenous, and intramuscular injection.

Due to the short half-life of αPEG Abs, intravenous administration is not a practical solution for long-term drug studies, as antibodies are eliminated within hours to days, requiring labor-intensive repeated injection of the animal model. Accordingly, in some embodiments, the αPEG Abs or compositions are not administered intravenously.

The αPEG Abs can be administered as the sole active agent or in combination with other agents. Diluting agents such as, but not limited to, saline phosphate buffers and water (including milli-Q water) can be used to allow for control of the antibody concentration within an injectable volume. Adjuvants such as, aluminum salts and nanoparticles/nanocarriers can be employed to enhance the antibody response. Multivalent or bispecific antibodies can also be used. Adjuvants, nanocarriers/nanoparticles, multivalent or bispecific antibodies can also possibly be used to decrease the required antibody dose.

In some embodiments, the anti-PEG antibodies (αPEG Abs) administered to the animal model are αPEG immunoglobulin M (IgM) or G (IgG). IgM is associated with the primary immune response, appearing upon the first exposure to an antigen, while IgG appears later, and can be associated with a secondary antigen exposure. In some embodiments, monoclonal anti-PEG antibodies are administered subcutaneously. For example, suitable anti-PEG antibodies (αPEG Abs) are commercially available. Commercially available anti-PEG antibodies include anti-PEG monoclonal antibody, clone 1D9-6 available from Life Diagnostics, monoclonal mouse PEG antibody, clone 5E10E9 available from LSBio, anti-polyethylene glycol antibody, clone 5D6-3 available from Abcam, and anti-polyethylene glycol antibody, clone 09F02 available from Abcam. In one embodiment, the αPEG Abs is an anti-PEG monoclonal antibody, clone 1D9-6 available from Life Diagnostics, Inc.

In another embodiment, the anti-PEG antibodies may be polyclonal antibodies derived from an animal allogenic to the animal model, and preferably having matched MHC molecules. Polyclonal antibodies can also be commercially obtained. In another embodiment, anti-PEG antibodies can be isolated from an allogeneic animal and then injected into the animal model. Suitable methods of inducing anti-PEG antibodies in an animal are known in the art including initial injection and booster injections.

In some embodiments, the anti-PEG antibodies are administered so the animal model has a detectable anti-PEG antibody concentration of at least 44 ng/ml. In some embodiments, the anti-PEG antibodies concentrations are from 44 ng/ml to 62 ng/ml. In some embodiments, the anti-PEG antibodies are at a level of 48 ng/ml to 55 ng/ml. In some embodiments, the anti-PEG antibodies are at a level of 52 ng/ml.

Suitable amounts of the anti-PEG antibodies to induce these anti-PEG concentrations in the animal models is able to be determined by one skilled in the art. For example, in a mouse model, the model may be injected from about 15 µg/ml to about 100 µg/ml of the antibodies subcutaneously.

For larger animals, additional amounts of antibodies may be needed, and can be calculated based on the mouse model, and one skilled in the art.

The animal model may suitably be any mammalian animal that is used in medical research. In some embodiments, the animal model is a non-genetically modified animal or a genetically modified animal. In some embodiments, the animal mode is not genetically modified. Suitable mammals include, for example, mice, rats, rabbits, chickens, goats, guinea pigs, hamsters, horses, mice, rats, and sheep. In some embodiments, the animal model is a mouse. For example, the animal model may be commercially available animals, for example, commercially available mice that are available from commercial suppliers, such as Jackson Laboratories, Charles River Laboratories, International, Laboratory Corporation of America Holdings, among others. For example, suitable mouse models include C57BL/6J or Balb/c mice available from Jackson Laboratory.

In the method of the present disclosure, the animal model is administered subcutaneously a composition comprising antibodies against one or more poly(ethylene glycol) chains, and maintains anti-PEG antibodies within the animal model for at least two days, preferably at least four days, preferably at least 6 days, preferably at least 10 days. Depending on the model parameters, including anti-PEG antibody dose, target anti-PEG antibody concentration, range of anti-PEG antibody concentration, and type of model (single injection or multiple injection), the amount of time that the model can be maintain is determined. For the single injection model, the model can be maintained for 2 to 30 days. In the embodiment where a single 100 µg/kg anti-PEG antibody is injected, for a model mimicking the general population as found by Yang et al., where the target anti-PEG antibody concentration is 52 ng/ml and the confidence interval is between 44 and 62 ng/ml, the model can be used for experimentation for 6 days during the period from 38 days to 44 days after initial subcutaneous injection (FIG. 5). With the same target parameters, an injection dose of 50 µg/kg also allows for an experimental phase of 6 days occurring from 28 days to 34 days after initial injection (FIG. 5). For the multiple injection model, the antibody concentration can be maintained for the lifetime of the animal as long as the booster injection occur.

The method may further comprise a step of administering one or more booster injections subcutaneously to the animal model after the first inject, the booster injections at least 14 days after the initial injection.

The present disclosure also describes methods of making in vivo models for detecting anti-poly(ethylene glycol) (PEG) antibodies (αPEG Abs), the method comprising (a) administering subcutaneously to an animal model a composition comprising antibodies against one or more poly(ethylene glycol) chains with a molecular weight with a molecular weight of at least 550 Da; (b) administering one or more booster injections subcutaneously at least 14 days after step (a); and (c) detecting anti-PEG antibodies within the animal model at a level of at least 44 ng/ml, wherein the in vivo animal model can be used to test compositions for the ability to produce anti-PEG antibodies.

In some embodiments, the anti-PEG antibodies are administered so the animal model has a detectable anti-PEG antibody concentration of at least 44 ng/ml that is maintained for at least 2 days, alternatively for at least 4 days, alternatively for at least 6 days, alternatively for at least 10 days. In some embodiments, the anti-PEG antibodies concentrations are from 44 ng/ml to 62 ng/ml. In some embodiments, the anti-PEG antibodies are at a level of 48 ng/ml to 55 ng/ml. In some embodiments, the anti-PEG antibodies are at a level of 52 ng/ml.

In some embodiments, the animal model has a target concentration of anti-PEG antibodies. In some embodiments, the target concentration has an upper bound. The "upper bound" refers to the upper most acceptable limit of antibody concentration in the animal model. In some embodiments, the target concentration has a lower bound. The "lower bound" refers to the lower most acceptable limit of antibody concentration in the animal model. In some embodiments, the lower bound is about 40 ng/ml, preferably about 44 ng/ml. In some embodiments, the upper bound in about 100 ng/ml, preferably about 65 ng/ml. Suitable amounts and ranges in-between are contemplated and may be useful in the methods of testing described herein.

In some embodiments, the animal model receives one or more booster subcutaneous injections such that the animal model maintains an antibody concentration within 10% of the target concentration. In some embodiments, the booster injections have a lower dose of anti-PEG antibodies compared to the initial anti-PEG antibodies subcutaneous injection(s). In some embodiments, the booster(s) dose(s) is equal to half of the initial loading dose. For example, in some embodiments, a booster dose of 3.6 µg/kg is given every 3 days after an initial loading dose of 7.2 µg/kg. In some embodiments, the booster(s) dose(s) is equal to one-fourth of the initial loading dose. One skilled in the are will be able to calculate a proper booster dose to maintain the levels of anti-PEG antibodies within the model.

In some embodiments, the booster injections maintain a detectable anti-PEG antibody concentration of at least 44±4.4 ng/ml. In some embodiments, the booster injections maintain a detectable anti-PEG antibody concentration of from 44±4.4 ng/ml to 62±6.2 ng/ml. In some embodiments, the booster injections maintain a detectable anti-PEG antibody concentration of from 48±4.8 ng/ml to 55±5.5 ng/ml. In some embodiments, the anti-PEG antibodies are at a level of about 52±5.2 ng/ml.

In some embodiments, the animal model receives one or more booster injections 3 days, 7 days, or 14 days after the initial injection. In some embodiments, the booster injections continue indefinitely for the lifetime of the model or the animal model.

The present disclosure also provides in some embodiments methods for testing an adjuvant/stimulatory molecule in the in vivo animal model described herein, suitably wherein the adjuvant or stimulatory molecule is a PEGylated compound or PEG-based nanoparticle or nanocarrier. An adjuvant is an agent that improves the immune response to a vaccine, e.g., an antigenic peptide or protein. Suitable adjuvants are known in the art. For example, adjuvants may include, but are not limited to, PEGylated compounds or PEG-based nanoparticles/nanocarriers. The method comprises administering the adjuvant to the animal model described herein, and monitoring the immune reaction to the adjuvant in the animal model as compared to a control animal model.

The term control or control animal model, as used herein, refers to an animal model that does not contain anti-PEG antibodies. For example, it may be a mouse of the same strain as the animal model described herein but without the antibody subcutaneous injections.

The methods described herein may be used for testing and screening of commercially available drugs for alterations in their effective dose, pharmacokinetics and/or biodistribution, immunogenicity, or potential adverse reactions when the drugs are in the presence of anti-PEG antibodies. The method comprise establishing the in vivo animal model having anti-PEG antibodies of at least 44 ng/ml, and administering the drug in an effective dose. The in vivo animal model is then monitored over time for changes in the pharmacokinetics, biodistribution, immunogenicity or potential adverse reaction in a model having anti-PEG antibodies, when compared to an animal model without such antibodies. Suitable methods of monitoring the pharmacokinetics, biodistribution, immunogenicity and adverse reactions are known and understood by one skilled in the art.

The methods described herein may also be used to screen new PEG-based therapeutics for alterations in their effective dose, pharmacokinetics and/or biodistribution, immunogenicity, or potential adverse reactions. The methods comprise administering the new PEG-based therapeutics to the in vivo animal model described herein, and monitoring the effects of therapeutic in the animal model on the effective dose, pharmacokinetics and/or biodistribution, immunogenicity, or potential adverse reactions as compared to a control model. The in vivo animal model can be monitored over time (i.e., days, weeks, etc.) for changes in the pharmacokinetics, biodistribution, immunogenicity or potential adverse reaction in a model having anti-PEG antibodies, when compared to an animal model without such antibodies (e.g., control animal model).

The methods described herein may also be used for screening PEG-based nanoparticle/nanocarrier platforms for alterations in their effective dose, pharmacokinetics and/or biodistribution, immunogenicity, or potential adverse reactions when they are in the presence of anti-PEG antibodies. The methods comprise administering the new PEG-based nanoparticle/nanocarrier to the in vivo animal model described herein, and monitoring the effects in the animal model on the effective dose, pharmacokinetics and/or biodistribution, immunogenicity, or potential adverse reactions as compared to a normal control. The in vivo animal model can be monitored over time (i.e., days, weeks, etc.) for changes in the pharmacokinetics, biodistribution, immunogenicity or potential adverse reaction in a model having anti-PEG antibodies, when compared to an animal model without such antibodies.

The methods described herein may also be used for screening or testing PEGylated devices for immunogenicity when they are administered to a subject having anti-PEG antibodies. Suitably, the PEGylated devices may be contacted or administered to the in vivo anti-PEG antibody model described herein and then the animal monitored as compared to a control animal model. Suitable methods of measuring the pharmacokinetics and biodistribution and immunogenicity are known in the art. The administering can be topical, oral or implantation within the animal model.

The methods described herein may also be used for screening PEG-containing food products for potential adverse reactions when they are ingested by a subject having anti-PEG antibodies. The methods comprise administering (e.g., orally) or feeding the PEG-containing food products to the animal model described herein, and monitoring the animal for adverse reactions as compared to a control animal (e.g., animal without anti-PEG antibodies). The food products are preferentially administered orally.

The methods described herein may also be used for screening PEG-containing personal care products for potential adverse reactions when they are contacted with a subject having anti-PEG antibodies. The methods include contacting the animal model described herein with the personal care product, preferentially, topically, and then observing or testing for an adverse reactions as compared to a control animal.

The methods described herein may also be used for screening PEG-containing cosmetic products for potential adverse reactions when they are administered to a subject that has of anti-PEG antibodies. The methods include contacting the animal model described herein with the cosmetics, preferentially, topically, and then observing or testing an adverse reactions as compared to a control animal.

The methods described herein may also be used for screening PEG-containing cleaning products for potential adverse reactions when they are in contact with a subject who has anti-PEG antibodies. The method comprises contacting the PEG-containing cleaning product to the animal model described herein, and monitoring the adverse reactions to the cleaning product. Preferably, the contacting is topical or skin contacting. In other embodiments, the contacting may be to a mucosal membrane.

Monitoring may be done by known methods in the art, for example, in visual observations of the skin of the subject contacted with the product or drug. Monitoring may also be by taking blood samples from the animal model and monitoring the level of one or more components within the blood sample, as compared to a control (e.g., animal model without anti-PEG antibodies).

The methods described herein may also be used for understanding how variations in anti-PEG antibody concentrations within various populations impact alterations in effective dose, pharmacokinetics and/or biodistribution, immunogenicity, or potential adverse reactions. This may be done by administering levels of the antibodies within the animal model when administered different compositions or drugs.

Suitably, the drugs, compositions or nanocarriers being tested using the animal models described herein include PEG chains. Many different PEG chains are contemplated to be able to be tested using the methods described herein.

Figure 6:
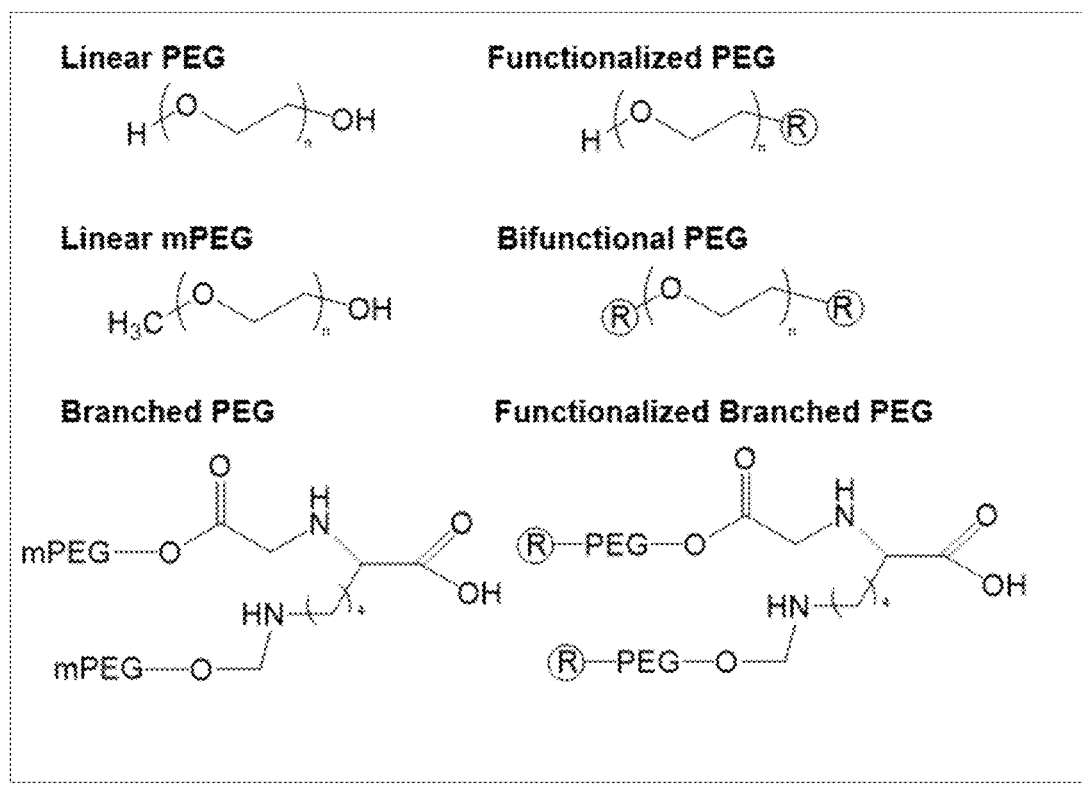
FIG. 6 is a depiction of various PEG structures, including commonly used PEG architectures and functionalization. R represents a functional group.

Poly(ethylene glycol) (PEG) is a polymer composed of various conformations of ethylene oxide monomers. These conformations consist of both linear and branched polymer chains and result in various molecular weights [1]-[3], see, e.g. FIG. 6. Accordingly, in some embodiments the PEG chains being tested have a molecular weight of at least 550 Da (550 g/mol). In some embodiments, the PEG chains have a molecular weight of from 550 Da to 8 million Da. In some embodiments, the PEG chains have a molecular weight of from 550 Da to 40 kDa (40,000 Da; 40,000 g/mol). In some embodiments, the PEG chains have a molecular weight of from 1 kDa to 20 kDa.

The specificity of the model in regards to molecular weight of the PEG is dependent on the specificity of the anti-PEG antibody administered to the model. In some embodiments, anti-PEG monoclonal antibody, clone 1D9-6 available from Life Diagnostics, Inc., which is specific to PEG chains with a molecular weight greater than 550 Da.

PEG chains can be covalently attached to the surface of a drug or material of choice in a technique called PEGylation [4], [5]. After PEGylation, a steric shield forms around the PEGylated substance.

Due to the unique properties conferred by PEGylation, PEG has become the go-to biomaterial to enhance delivery of therapeutic molecules [11]. As of 2020, there were 21 PEGylated drugs approved by the FDA, and over 20 others in active clinical trials [12], [13]. These drugs include PEGylated enzymes, proteins, and liposomes, which are used in the treatment of several diseases such as cancer, autoimmune diseases, and genetic disorders [12], [13]. Approved therapeutics contain PEG molecules spanning from less than 1 kDa to 40 kDa in molecular weight (Table 1) [12], [13].

TABLE 1

PEGylated drugs approved by the FDA. Adapted from [12], [13].

| Brand Name | Generic Name | Indication | PEGylated Molecule | PEG Size (kDa) | # PEG chains | Year Approved |
|---|---|---|---|---|---|---|
| Adagen | Pegdamase bovine | Severe combined immunodeficiency disease | enzyme | 5 | 11-17 | 1990 |
| Oncaspar | Pegasparginase | Acute lymphoblastic leukemia | enzyme | 5 | 69-82 | 1994 |
| Doxil | Doxorubicin hydrochloride liposome | Ovarian cancer, AIDS-related Kaposi's Sarcoma, multiple myeloma | liposome | 2 | n/a | 1995 |
| Onivyde | Irinotecan liposome | Metastatic adenocarcinoma of the pancreas | liposome | 2 | n/a | 1996 |
| Pegasys | Peginterferon alfa-2a | Hepatitis B, C chronic | protein | 40 | 1 | 2001 |
| PegIntron | Peginterferon alfa-2b | Hepatitis C, chronic | protein | 12 | 1 | 2001 |
| Neulasta | Pegfilgratim | Neutropenia, hematopoietic sub-syndrome of acute radiation syndrome | protein | 20 | 1 | 2002 |
| Somavert | Pegvisomant | Acromegaly | protein | 5 | 4-6 | 2003 |
| Macugen | Pegaptanib | Neovascular age-related macular degeneration | aptamer | 20 | 2 | 2004 |
| Mircera | mPEG-epoetin beta | Anemia associated with chronic kidney disease | protein | 30 | 1 | 2007 |
| Cimzia | Certolizumab pegol | Crohn's disease, rheumatoid arthritis, psoriatic arthritis, ankylosing spondylitis | FAB fragment | 40 | 1 | 2008 |
| Krystexxa | Pegloticase | Gout | enzyme | 10 | 36 | 2010 |
| Sylatron | Peginterferon alfa-2b | Melanoma | protein | 12 | 1 | 2011 |
| Omontys | Peginesatide | Anemia associated with chronic kidney disease | peptide | 40 | 1 | 2012 |
| Movanik | Naloxegol | Opioid-induced constipation | small molecule | <1 | 1 | 2014 |
| Plegridy | Peginterferon beta-1a | Multiple sclerosis | protein | 20 | 1 | 2014 |
| Adynovate | Antihemophilic factor, PEGylated | Hemophilia A | protein | 20 | 1 or more | 2015 |
| Rebinyn | Coagulation factor IC, glyco-PEGylated | Hemophilia B | protein | 40 | 1 | 2017 |
| Asparlas | Calaspargase pegol | Acute lymphoblastic leukemia | enzyme | 5 | 31-39 | 2018 |
| Palynziq | Pegvaliase | Phenylketonuria | enzyme | 20 | 9 | 2018 |
| Revcovi | Elapegademase | Adenosine deaminase combined immunodeficiency | enzyme severe | 5.6 | 13 | 2018 |

In addition to the use of PEG in therapeutics, the polymer is extensively used as a solvent and emulsifying agent in household products[12]. PEG can be found in everyday products such as shampoo, moisturizer, makeup and soaps, and in topological agents[12]. The prevalence of PEG in products highly utilized by society has significantly increased in the past decades, with a growing variety of chain sizes, structures and functional groups used in common products[12].

Although it had been initially thought that PEG had non-immunogenic properties[5], anti-PEG antibodies (αPEG Abs) were first observed in rabbits following immunization with PEGylated ovalbumin[13]. One year later, levels of pre-existing αPEG Abs were first detected in blood donors without previous exposure to PEGylated therapeutics[14]. The development of αPEG Abs in humans is associated with exposure to PEG-containing products on a daily basis[6]. These antibodies are known as "pre-existing" antibodies[6]. A 2016 study found that 72% of people without prior exposure to PEG-based drugs carry detectable concentrations of αPEG Abs[6]. The study found that the average αPEG Abs immunoglobulin G concentration was 52 ng/ml in the general population[6]. With the presence of pre-existing αPEG Abs, patients receiving treatment with a PEGylated drug can experience accelerated blood clearance, pharmacokinetic changes with multiple does, decreased therapeutic function due to decreased therapeutic circulation time, and anaphylaxis[6,14].

In some embodiments, the method further comprises screening PEGylated compounds, PEG-modified compound, and/or PEG-containing products. In some embodiments, the screening of PEGylated compounds, PEG-modified compound, and/or PEG-containing products may refer to measuring the levels of anti-PEG antibodies before and after the administration or contact with the PEGylated compounds, PEG-modified compound, and/or PEG-containing products. In some embodiments, the screening of PEGylated compounds or PEG-modified compounds, may be measuring changes in the effective dose of said PEGylated compounds or PEG-modified compound when in the presence of anti-PEG antibodies. In some embodiments, the screening of PEGylated compounds or PEG-modified compounds, may be measuring changes in the pharmacokinetics and/or biodistribution of said PEGylated compounds or PEG-modified compound when in the presence of anti-PEG antibodies. In some embodiments, the screening of PEGylated compounds or PEG-modified compounds, may be measuring changes in the immunogenicity of said PEGylated compounds or PEG-modified compound when in the presence of anti-PEG antibodies.

In further embodiments, the in vivo animal model may be used to monitor the immune response to PEGylated drugs, compounds, PEG-containing nanocarriers and PEG-products that may be administered or come into contact with a subject. The animal model herein comprises anti-PEG antibodies, and the ability of these antibodies to recognize PEG-containing products and to elicit an immune response to the PEG-containing products can be monitored. For example, an antibody-mediated immune response can be detected and monitored using the animal model described herein using methods known in the art.

PEGylated compounds or PEG-modified compounds may be, but are not limited to, PEGylated enzymes, PEGylated proteins, PEGylated liposomes, PEGylated aptamers, PEGylated peptides, or PEGylated small molecules. The PEGylated compounds to be screened in the method of the present disclosure include, but are not limited to, the compounds disclosed in Table 1.

PEG-containing products may be, but are not limited to, shampoo, moisturizers, makeup, and soap. In 1992, product formulation data reported to the FDA showed that 7 structures of PEG, varying in molecular weight, polymer architecture and functionalization, could be found in 262 different commercially available cosmetic formulations [2]. By 2015, the number of PEG structural variations of PEG found in cosmetic products had increased drastically to over 340 structures [12]. Structures vary in molecular weight, physical structure and/or architecture (linear, branched), and chemical functionalization.

The use herein of the terms "including," "comprising," or "having," and variations thereof, is meant to encompass the elements listed thereafter and equivalents thereof as well as additional elements. Embodiments recited as "including," "comprising" or "having" certain elements are also contemplated as "consisting essentially of" and "consisting of" those certain elements.

As used herein, "about" means within 5-10% of a stated concentration range or within 5-10% of a stated number.

It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements. The term "consisting essentially of" and "consisting of" should be interpreted in line with the MPEP and relevant Federal Circuit's interpretation. The transitional phrase "consisting essentially of" limits the scope of a claim to the specified materials or steps "and those that do not materially affect the basic and novel characteristic(s)" of the claimed invention. "Consisting of" is a closed term that excludes any element, step or ingredient not specified in the claim. The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of" will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of" "only one of," or "exactly one of."

The present invention has been described in terms of one or more preferred embodiments, and it should be appreciated that many equivalents, alternatives, variations, and modifications, aside from those expressly stated, are possible and within the scope of the invention.

The following Examples are offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

Example 1

Introduction

Poly(ethylene glycol) (PEG) is a non-toxic, hydrophilic polymer composed of ethylene oxide monomers that can be combined into linear or branched polymer chains with various molecular weight[1,2]. Over the past 40 years, PEG has shown great potential to overcome rapid clearance, low solubility, and high immunogenicity associated with peptide, protein, and small molecule drug delivery, and has therefore gained the attention of drug companies and researchers[3-5]. PEG can be used as an excipient, a drug carrier, or as a coating agent[6]. Through a technique called PEGylation, PEG chains are covalently attached to the surface of a drug or material of choice[3,7]. Each PEG polymer subunit associates with two to three water molecules; the hydrated polymer shields the therapeutic from immunogenic recognition by neutralizing antibodies and the degradative action of proteolytic enzymes [5], [8]. Additionally, PEGylation increases the hydrodynamic diameter (HD) and molecular weight of PEGylated moiety, thereby limiting renal clearance and increasing circulation times. This is particularly useful for nanosized therapeutics, as glomerular filtration depends heavily on the size and molecular weight of a particle due to the structure and permeability of the glomerulus[8]. Hence, particles with a hydrodynamic diameter (HD) larger than 8 nm cannot be filtrated and eliminated by the kidneys[8]. Due its unique properties, PEG has become the go-to biomaterial to enhance delivery of therapeutic molecules[9]. As of 2020, there were 21 PEGylated drugs approved by the FDA, and over 20 others in active clinical trials[10,11].

In addition to the use of PEG in therapeutics, the polymer is extensively used as a solvent and emulsifying agent in household products[12]. PEG can be found in everyday products such as shampoo, moisturizer, makeup and soaps, and in topological agents[12]. The prevalence of PEG in products highly utilized by society has significantly increased in the past decades, with a growing variety of chain sizes, structures and functional groups used in common products[12].

Although it had been initially thought that PEG had non-immunogenic properties[5], anti-PEG antibodies (αPEG Abs) were first observed in rabbits following immunization with PEGylated ovalbumin[13]. One year later, levels of pre-existing αPEG Abs were first detected in blood donors without previous exposure to PEGylated therapeutics[14]. The development of αPEG Abs in humans is associated with exposure to PEG-containing products on a daily basis[6]. These antibodies are known as "pre-existing" antibodies[6]. A 2016 study found that 72% of people without prior exposure to PEG-based drugs carry detectable concentrations of αPEG Abs[6]. The study found that the average αPEG Abs immunoglobulin G concentration was 52 ng/ml in the general population[6]. With the presence of pre-existing αPEG Abs, patients receiving treatment with a PEGylated drug can experience accelerated blood clearance, pharmacokinetic changes with multiple does, decreased therapeutic function due to decreased therapeutic circulation time, and anaphylaxis[6,14].

During the drug development process, PEG containing drugs are assessed using animal models that are shielded from the PEG exposure common to daily human life. When novel drugs reach human trials, unexpected results, including inefficacy and adverse reactions, have occurred due to the presence of αPEG Abs in human blood. For example, in a 2013 Phase 2b clinical trial of Pegnivocagin, a PEGylated RNA aptamer for the inhibition of coagulation factor Ixa, patients with pre-existing αPEG Abs developed anaphylactic and skin reactions, resulting in the termination of the trial.[15,16]

Failure of drugs in human clinical trials pose a great financial and health burden on society. Bring a drug from development to the market is estimated to exceed $2.5 billion[17]. Risk of failure in clinical trials is high—averaging 95%[18]. Most critically, dire health outcomes may result from adverse drug effects[17,19]. Eliminating drug candidates that will fail in clinical trials before economic effect and human health are put at risk is vital for society[17,19].

Thus, there is a great need for an animal model to recapitulate concentrations of αPEG Abs found in human blood to assess novel therapeutics prior to human trial. A variety of approaches have been described in literature to create αPEG Abs animal models. Mouse models are ideal due to their commonality in research, low cost and small size[20]. Passive transfer (PT) models consist of exposing animals to highly characterized, commercially available monoclonal antibodies. Previous PT models utilize the intravenous (IV) route of administration[21]. However, none have successfully captured the state of pre-existing αPEG Abs known to be present in the general population at relevant concentrations.

Due to the short half-life of αPEG Abs, IV PT models are not a practical solution for long-term drug studies, as antibodies are eliminated within hours to days, requiring labor-intensive repeated injection of the animals[21]. Herein, we utilize subcutaneous injection to extend the half-life of PT αPEG Abs and enhance ease of model maintenance, in terms of both improved ease of injection method and reduced frequency of injection.

A final issue with existing αPEG Abs is the ability of these mouse models to successfully recapitulate the steady state concentration of αPEG Abs for an extended duration of time in order to test PEG-based therapeutics[22]. Ideally, steady state maintenance of multiple concentrations of αPEG Abs by different cohorts of mice would be achieved. This would allow PEG-based therapeutics to be assessed on organisms with different blood concentrations of Abs to account for Ab variations in the general population[6]. This would be impactful as it has been previously seen that some drugs are safe and effective for patients with low αPEG Abs, but extremely dangerous for patients with high Ab concentration. To the best of our knowledge, this work presents the first attempt to use subcutaneous injection for the PT αPEG Abs. With this strategy, we have developed a mouse models for the rigor assessment of PEG-based therapeutics.

Methods and Materials

Animals 8 to 12-week-old, male C57BL/6J mice were purchased from Jackson Labs. Mice were housed in the Center for Comparative Medicine (CCM) at Northwestern University. All animal protocols were approved by Northwestern University's Institutional Animal Care and Use Committee (IACUC).

ELISA

An in-house enzyme-linked immunosorbent assay (ELISA) was developed to quantify the concentration of anti-PEG IgG in mouse blood samples. Amine-coated 96-well plates (Life Science) were incubated with a 4 mM N-Hydroxysuccinimide-mPEG 5 kDa, 10 kDa or 20 kDa (Nanocs) solution for 45 minutes at 37° C. The wells were washed with PEG Wash Buffer (Life Diagnostics) and blotted three times. Plates were blocked overnight with 125 ul of PEG blocking buffer (Life Diagnostics, Inc.) per well and washing was repeated. Standards of known anti-PEG IgG concentration (0-200 ng/ml) were made by diluting backbone specific anti-PEG monoclonal antibody, clone 1D9-6 (Life Diagnostics, Inc.) in whole mouse blood. Both solutions of unknown and known concentrations were diluted by half with PEG Blocking Buffer (Life Diagnostics, Inc.). 100 µl of each solution was plated and incubated at room temperature for 2 hours with mild agitation. The wells were then washed and blotted five times. Goat anti-mouse IgG (H+L) horseradish peroxidase (HRP) secondary antibody (Sigma) was diluted in PEG Blocking Buffer in a 1:3000 dilution. 50 µl of the resulting solution was plated and incubated at room temperature for 45 minutes. The wells were then washed and blotted five times. Finally, the plate was incubated with 50 µl tetramethylbenzidine (Sigma), and after 15 minutes, 50 µl of 0.2 M sulfuric acid (Fisher) was added to each well. The absorbance of each well was read at 450 nm on a Cytation 5 (BioTek). Absorbance was related to concentration to determine concentration of anti-PEG IgG of samples with unknown concentrations.

Passive Transfer

Mice were subcutaneously injected with backbone specific anti-PEG monoclonal antibody, clone 1D9-6 (Life Diagnostics, Inc.). The animals were sacrificed at specific timepoints after the injection(s) and underwent blood collection through cardiac puncture.

Results and Discussion

FIG. 1 shows that intravenous passive transfer of anti-PEG antibodies results in rapid clearance. Mice were intravenously injected with 7.5 μg/kg of anti-PEG antibodies. Antibody concentration was assessed via ELISA at various time points. The t-max was found to be 0.5 h at an average concentration of 61 ng/ml. The half-life of the antibody was determined to be 10.78 h. The requirement to inject mice approximately every 11 h would not be feasible for most studies due to the labor-intensive nature of the injection interval.

Figure 2:
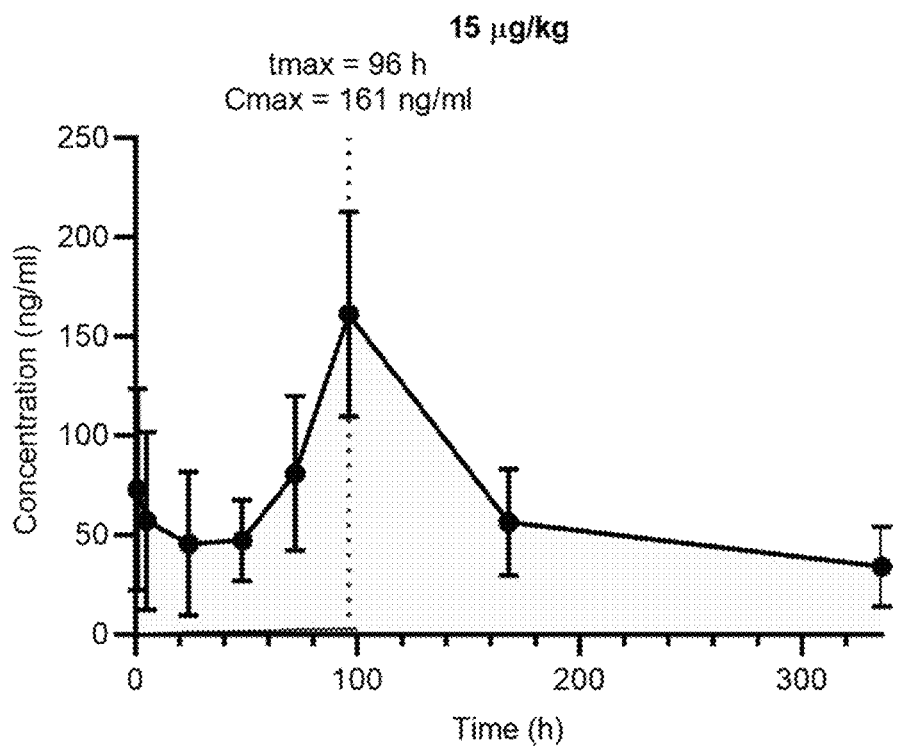
FIG. 2 are graphs showing the concentration of anti-PEG IgG antibodies in mice injected subcutaneously with anti-PEG antibodies at doses of 15 μg/kg (top) or 100 μg/kg (bottom), assessed via ELISA, as a function of time. Top: With a single dose of 15 μg/kg, the maximum concentration of anti-PEG IgG antibody in whole blood is 161 ng/ml achieved 96 h post-injection. (n=5). Bottom: With a single dose of 100 μg/kg, the maximum concentration of anti-PEG IgG antibody in whole blood is 333 ng/ml achieved 24 h post-injection. (n=5).
Figure 2:
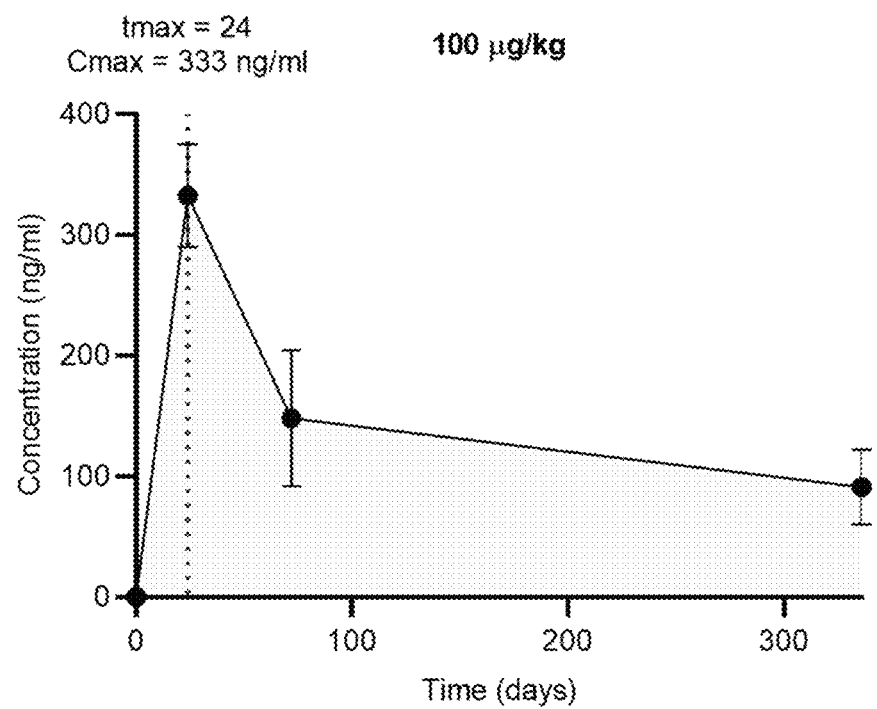

FIG. 2 shows that subcutaneous passive transfer of anti-PEG antibodies reduces clearance. Mice were subcutaneously injected with 15 μg/kg (FIG. 2 top) or 100 μg/kg (FIG. 2 bottom) of anti-PEG antibodies. Antibody concentration in whole blood was assessed via ELISA at various time points. Altering the dose of anti-PEG antibodies allows for altered kinetics. A dose of 15 μg/kg results in a tmax of 4 days at an average concentration of 161 ng/ml, while a dose of 100 μg/kg results in a tmax of 1 day at 333 ng/ml.

FIG. 5 shows that a single subcutaneous can be used to maintain a desired range of antibody concentration over a period of time. Mice were subcutaneously injected with 50 or 100 μg/kg of anti-PEG antibodies. Antibody concentration in whole blood was assessed via ELISA at various time points. Following subcutaneous injection, an induction period occurs, during which the antibody concentration is above the desired range. In the case of a 100 μg/kg injection, this period is from day 0 to 38. The experimental phase starts on day 38 and runs through day 44. During this 6 day period, the antibody concentration is well within the defined range. During this period (experimental phase) experiments should be conduction. From day 44 and onward, the extinguished phase occurs. The antibody concentration has fallen below the defined range. Thus, no experimentation should occur. See section below for definitions and further explanation of parameters.

Figure 3:
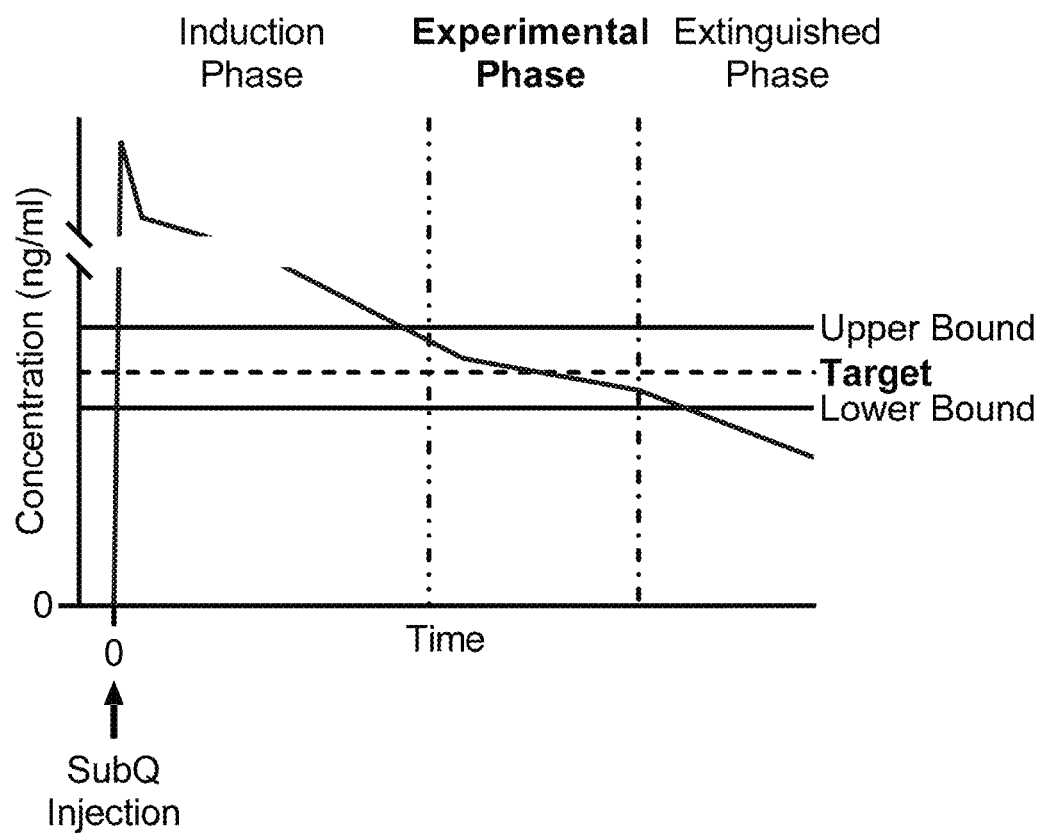
FIG. 3 is a graphical illustration of the Single Injection Model. Anti-PEG antibody concentration is shown as a function of time after a single initial subcutaneous injection. To utilize the single injection model, a target concentration of anti-PEG antibody must be defined as the target. Either immunoglobulin M (IgM) or immunoglobulin G (IgG) antibodies can be modeled. Furthermore, an upper most acceptable limit of antibody concentration must be identified. This is referred to as the upper bound. Likewise, a lower most acceptable limit of antibody concentration must be identified; this is known as the lower bound. The model consists of three phases: induction, experimental and extinguished. The induction phase is defined as the time from initial subcutaneous injection until antibody concentrations are below the upper bound by 10% of the target. Following subcutaneous injection, the antibody concentration will rise quickly above the upper bound to a peak. After which, the antibody concentration will decline. During this period, no experimentation should occur. When antibody concentration goes below the upper bound, the model transition into the experimental phase. During the experimental phase, the antibody concentration should be less than the upper bound and greater than the lower bound. The entity of the experimentation should take place within this phase to ensure the targeted antibody concentration is maintained. During the experimental phase, the antibody concentration will decrease, but at a lower rate than during the induction phase. When the antibody concentration reaches a concentration that is equal to 10% of the target greater than the lower bound, the extinguished phased starts. During this phase, no experiments should be conducted. The antibody levels continue to fall. The animals should be humanely sacrificed or used for an unrelated purpose.

Single Injection Model (FIG. 3)

Establishing Parameters for Single Injection Model

To utilize the single injection model, a target concentration of anti-PEG antibody must be defined as the target. Either immunoglobulin M (IgM) or immunoglobulin G (IgG) antibodies can be modeled. Furthermore, an upper most acceptable limit of antibody concentration must be identified. This is referred to as the upper bound. Likewise, a lower most acceptable limit of antibody concentration must be identified; this is known as the lower bound. Previously, the target has been defined as the geometric mean concentration of anti-PEG antibodies in the general population as identified by Yang et al (for IgG 52 ng/ml)[6]. The lower and upper bounds have been defined as the 95% confidence interval of that mean for IgG (for IgG 44 ng/ml and 62 ng/ml, respectively)[6]. It should be noted that the average concentration of anti-PEG antibodies in the general population may change over time. Of note, due to the prevalence of PEG in consumer products, the concentration has increased substantially over the past 4 decades[6]. Thus, it may be desirable to change the target, lower bound and upper bound over time. Additionally, the target may be changed to model a specific population with a corresponding known anti-PEG antibody concentration (for example: PEG antibody positive population, high PEG consumers, low PEG consumers, etc.).

Model Phases for Single Injection Model

The model consists of three phases: induction, experimental and extinguished. The induction phase is defined as the time from initial subcutaneous injection until antibody concentrations are below the upper bound by 10% of the target. For example, if our target is 52 ng/ml and our upper bound is 62 ng/ml, the induction phase ends when the antibody concentration reaches approximately 57 ng/ml. The rationale for the use of the 10% buffer is to account for variability between mice and limitations of antibody detection. Following subcutaneous injection, the antibody concentration will rise quickly above the upper bound to a peak. After which, the antibody concentration will decline. During this period, no experimentation should occur. When antibody concentration goes below the upper bound, the model transition into the experimental phase. During the experimental phase, the antibody concentration should be less than the upper bound and greater than the lower bound. The entity of the experimentation should take place within this phase to ensure the targeted antibody concentration is maintained. During the experimental phase, the antibody concentration will decrease, but at a lower rate than during the induction phase. When the antibody concentration reaches a concentration that is equal to 10% of the target greater than the lower bound, the extinguished phased starts. During this phase, no experiments should be conducted. The antibody levels continue to fall. The animals should be humanely sacrificed or used for an unrelated purpose.

Figure 4:
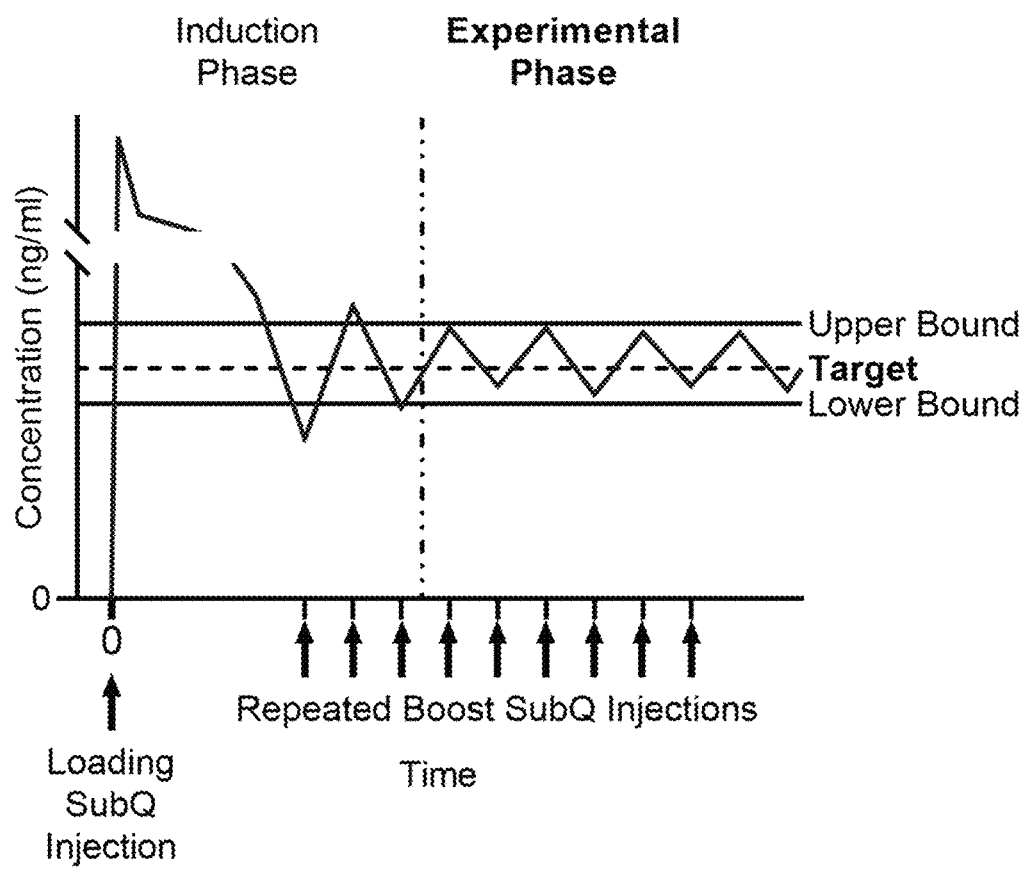
FIG. 4 is a graphical illustration of the Multiple Injection Model. Anti-PEG antibody concentration is shown as a function of time after a single initial subcutaneous injection and one or more boost injections. To utilize the multiple injection model, a target concentration of anti-PEG antibody must be defined as the target. Either immunoglobulin M (IgM) or immunoglobulin G (IgG) antibodies can be modeled. Furthermore, an upper most acceptable limit of antibody concentration must be identified. This is referred to as the upper bound. Likewise, a lower most acceptable limit of antibody concentration must be identified; this is known as the lower bound. The model consists of two phases: induction and experimental. The induction phase consists of a subcutaneous loading dose of anti-PEG antibody followed by at least one boost subcutaneous injection. However, generally it is advisable that multiple boosts are given during the induction phase to ensure the steady state of the antibody concentration. Generally, the loading dose is higher than the boost(s). During this phase the initial loading dose, may cause the antibody concentration to exceed the upper bound. After which, the antibody concentration should stabilize. No experiments should be conducted during this phase. The phase ends when the antibody concentration does not exceed the upper or lower bound by more than 10% of the target concentration. Ideally, transitions to the experimental phase occurs when the antibody concentration remains within the bounds. For some experimental conditions, it may not be possible to achieve concentrations within this defined range. In this case, the experimental phase may contain antibody concentrations exceeding the bounds on either side by less than 10%. defined as the time from initial subcutaneous injection until antibody concentrations are below the upper bound by 10% of the target. During this phase, repeated boost injections continue to be are at regular intervals. All experimentation occurs during this phase. Injections and experimentation can be conducted for the lifetime of the animal. The animals should be humanely sacrificed.

Multiple Injection Model (FIG. 4)

Establishing Parameters for Multiple Injection Model

To utilize the multiple injection model, a target concentration of anti-PEG antibody must be defined as the target. Either immunoglobulin M (IgM) or immunoglobulin G (IgG) antibodies can be modeled. Furthermore, an upper most acceptable limit of antibody concentration must be identified. This is referred to as the upper bound. Likewise, a lower most acceptable limit of antibody concentration must be identified; this is known as the lower bound. Previously, the target has been defined as the geometric mean concentration of anti-PEG antibodies in the general population as identified by Yang et al (for IgG 52 ng/ml)[6]. The lower and upper bounds have been defined as the 95% confidence interval of that mean for IgG (for IgG 44 ng/ml and 62 ng/ml, respectively)[6]. It should be noted that the average concentration of anti-PEG antibodies in the general population may change over time. Of note, due to the prevalence of PEG in consumer products, the concentration has increased substantially over the past 4 decades[6]. Thus, it may be desirable to change the target, lower bound and upper bound over time. Additionally, the target may be changed to model a specific population with a corresponding known anti-PEG antibody concentration (for example: PEG antibody positive population, high PEG consumers, low PEG consumers, etc.).

Model Phases for Multiple Injection Model

The model consists of two phases: induction and experimental. The induction phase consists of a subcutaneous loading dose of anti-PEG antibody followed by at least one boost subcutaneous injection. However, generally it is advisable that multiple boosts are given during the induction phase to ensure the steady state of the antibody concentration. Generally, the loading dose is higher than the boost(s). During this phase the initial loading dose, may cause the antibody concentration to exceed the upper bound. After which, the antibody concentration should stabilize. No experiments should be conducted during this phase. The phase ends when the antibody concentration does not exceed the upper or lower bound by more than 10% of the target concentration. Ideally, transitions to the experimental phase occurs when the antibody concentration remains within the bounds. For some experimental conditions, it may not be possible to achieve concentrations within this defined range. In this case, the experimental phase may contain antibody concentrations exceeding the bounds on either side by less than 10%. defined as the time from initial subcutaneous injection until antibody concentrations are below the upper bound by 10% of the target. During this phase, repeated boost injections continue to be are at regular intervals. All experimentation occurs during this phase. Injections and experimentation can be conducted for the lifetime of the animal. The animals should be humanely sacrificed.

REFERENCES FOR EXAMPLE 1

1. Fruijtier-Polloth, C. Safety assessment on polyethylene glycols (PEGs) and their derivatives as used in cosmetic products. *Toxicology* 214, 1-38, doi:10.1016/j.tox.2005.06.001 (2005).
2. Delgado, C., Francis, G. E. & Fisher, D. The uses and properties of PEG-linked proteins. *Crit Rev Ther Drug Carrier Syst* 9, 249-304 (1992).
3. Harris, J. M. & Chess, R. B. Effect of pegylation on pharmaceuticals. *Nat Rev Drug Discov* 2, 214-221, doi:10.1038/nrd1033 (2003).
4. Veronese, F. M. & Pasut, G. PEGylation, successful approach to drug delivery. *Drug Discov Today* 10, 1451-1458, doi:10.1016/S1359-6446(05)03575-0 (2005).
5. Abuchowski, A., van Es, T., Palczuk, N. C. & Davis, F. F. Alteration of immunological properties of bovine serum albumin by covalent attachment of polyethylene glycol. *J Biol Chem* 252, 3578-3581 (1977).
6. Yang, Q. et al. Analysis of Pre-existing IgG and IgM Antibodies against Polyethylene Glycol (PEG) in the General Population. *Anal Chem* 88, 11804-11812, doi:10.1021/acs.analchem.6b03437 (2016).
7. Harris, J. M., Martin, N. E. & Modi, M. Pegylation: a novel process for modifying pharmacokinetics. *Clin Pharmacokinet* 40, 539-551, doi:10.2165/00003088-200140070-00005 (2001).
8. Deen, W. M., Lazzara, M. J. & Myers, B. D. Structural determinants of glomerular permeability. *Am J Physiol Renal Physiol* 281, F579-596, doi:10.1152/ajprenal.2001.281.4.F579 (2001).
9. Hoang Thi, T. T. et al. The Importance of Poly(ethylene glycol) Alternatives for Overcoming PEG Immunogenicity in Drug Delivery and Bioconjugation. *Polymers (Basel)* 12, doi:10.3390/polym12020298 (2020).
10. Swierczewska, M., Lee, K. C. & Lee, S. What is the future of PEGylated therapies? *Expert Opin Emerg Drugs* 20, 531-536, doi:10.1517/14728214.2015.1113254 (2015).
11. Ramos-de-la-Peña, A. M. & Aguilar, O. Progress and Challenges in PEGylated Proteins Downstream Processing: A Review of the Last 8 Years. *Int. J. Pept. Res. Ther.* 26, 333-348, doi:10.1007/s10989-019-09840-4. (2020).
12. Jang, H. J., Shin, C. Y. & Kim, K. B. Safety Evaluation of Polyethylene Glycol (PEG) Compounds for Cosmetic Use. *Toxicol Res* 31, 105-136, doi:10.5487/TR.2015.31.2.105 (2015).
13. Richter, A. W. & Akerblom, E. Antibodies against polyethylene glycol produced in animals by immunization with monomethoxy polyethylene glycol modified proteins. *Int Arch Allergy Appl Immunol* 70, 124-131, doi:10.1159/000233309 (1983).
14. Richter, A. W. & Akerblom, E. Polyethylene glycol reactive antibodies in man: titer distribution in allergic patients treated with monomethoxy polyethylene glycol modified allergens or placebo, and in healthy blood donors. *Int Arch Allergy Appl Immunol* 74, 36-39, doi:10.1159/000233512 (1984).
15. Ganson, N. J. et al. Pre-existing anti-polyethylene glycol antibody linked to first-exposure allergic reactions to pegnivacogin, a PEGylated RNA aptamer. *J Allergy Clin Immunol* 137, 1610-1613 e1617, doi:10.1016/j.jaci.2015.10.034 (2016).
16. Povsic, T. J. et al. A Phase 2, randomized, partially blinded, active-controlled study assessing the efficacy and safety of variable anticoagulation reversal using the REG1 system in patients with acute coronary syndromes: results of the RADAR trial. *Eur Heart J* 34, 2481-2489, doi:10.1093/eurheartj/ehs232 (2013).
17. DiMasi, J. A., Grabowski, H. G. & Hansen, R. W. The cost of drug development. *N Engl J Med* 372, 1972, doi:10.1056/NEJMc1504317 (2015).
18. Hay, M., Thomas, D. W., Craighead, J. L., Economides, C. & Rosenthal, J. Clinical development success rates for investigational drugs. *Nat Biotechnol* 32, 40-51, doi:10.1038/nbt.2786 (2014).
19. Aad, G. et al. Search for Magnetic Monopoles and Stable High-Electric-Charge Objects in 13 Tev Proton-Proton Collisions with the ATLAS Detector. *Phys Rev Lett* 124, 031802, doi:10.1103/PhysRevLett.124.031802 (2020).
20. Vandamme, T. F. Use of rodents as models of human diseases. *J Pharm Bioallied Sci* 6, 2-9, doi:10.4103/0975-7406.124301 (2014).
21. Hsieh, M. J. et al. Comparative efficacy and tolerability of beclomethasone/formoterol and fluticasone/salmeterol fixed combination in Taiwanese asthmatic patients. *J Formos Med Assoc* 117, 1078-1085, doi:10.1016/j.jfma.2017.12.005 (2018).
22. Hsieh, Y. C. et al. Pre-existing anti-polyethylene glycol antibody reduces the therapeutic efficacy and pharmacokinetics of PEGylated liposomes. *Theranostics* 8, 3164-3175, doi:10.7150/thno.22164 (2018).

We claim:

1. A method of making an in vivo model for detecting and monitoring anti-poly(ethylene glycol) (PEG) antibodies and an immune response to antigens recognized by the anti-PEG antibodies, the method comprising:
    (a) administering subcutaneously to an animal model a composition comprising at least one commercially available antibody against poly(ethylene glycol) chains with a molecular weight of at least 550 Da, wherein the at least one commercially available antibody is selected from antibody clone 1D9-6, antibody clone 5E10E9, antibody clone 5D6-3, and antibody clone 09F02; and
    (b) detecting anti-PEG antibodies within the animal model at a level of at least 44 ng/ml.

2. The method of claim 1, wherein the anti-PEG antibodies within the animal model are at a level of 44 ng/ml to 62 ng/ml.

3. The method of claim 1, wherein the PEG chains have a molecular weight of from 550 Da to 40 kDa.

4. The method of claim 3, wherein the PEG chains have a molecular weight from 1 kDa to 20 kDa.

5. The method of claim 1, wherein the method further comprises administering to the animal model a PEGylated compound; and screening the animal model for changes in the PEGylated compound's effective dose, pharmacokinetics and/or biodistribution, or immunogenicity within the animal model as compared to a control animal model.

6. The method of claim 1, wherein the method further comprises administering to the animal model a PEG-based nanoparticle or nanocarrier and screening the animal model for changes in the PEG-based nanoparticle or nanocarrier's effective dose, pharmacokinetics, biodistribution, and/or immunogenicity as compared to a control animal model.

7. The method of claim 1, wherein the method further comprises contacting the animal model with a PEGylated device and screening the animal model for immunogenicity by monitoring the antibody and immune response in the animal model after contacting with the PEGylated device as compared with a control animal model.

8. The method of claim 1, wherein the method further comprises administering or contacting the animal model with a PEG-containing product, and monitoring the animal model for adverse reactions, wherein the PEG-containing product is selected from the group consisting of food, personal care, cosmetic, and cleaning products.

9. The method of claim 8, wherein the contacting or administering is topical administration.

10. The method of claim 1, wherein the method further comprises administering one or more booster injections subcutaneously at least 14 days after step (a); and detecting anti-PEG antibodies within the animal model at a level of at least 44 ng/ml, wherein the in vivo animal model can be used to test compositions for their reactivity to anti-PEG antibodies or altered immune response as compared with a control animal model.

11. A method of making an in vivo model for detecting anti-poly(ethylene glycol) (PEG) antibodies and an immune response to PEG-containing compounds recognized by the anti-PEG antibodies, the method comprising:
  (a) administering subcutaneously to an animal model a composition comprising at least one commercially available antibody against one or more poly(ethylene glycol) chains with a molecular weight of at least 550 Da, wherein the at least one commercially available antibody is selected from antibody clone 1D9-6, antibody clone 5E10E9, antibody clone 5D6-3, and antibody clone 09F02;
  (b) administering one or more booster injections subcutaneously at least 14 days after step (a); and
  (c) detecting anti-PEG antibodies within the animal model at a level of at least 44 ng/ml.

12. The method of claim 11, wherein the anti-PEG antibodies within the animal model are at a level of 44 ng/ml to 62 ng/ml.

13. The method of claim 11, wherein the PEG chains have a molecular weight of from 550 Da to 40 kDa.

14. The method of claim 13, wherein the PEG chains have a molecular weight from 1 kDa to 20 kDa.

15. The method of claim 11, wherein the method further comprises administering a PEGylated compound to the animal model and screening the animal model for changes in the PEGylated compound's effective dose, pharmacokinetics and/or biodistribution, or immunogenicity as compared to a control animal model.

16. The method of claim 11, wherein the method further comprises administering a PEG-based nanoparticle or nanocarrier to the animal model and monitoring the animal model for changes in the PEG-based nanoparticle or nanocarrier effective dose, pharmacokinetics and/or biodistribution, or immunogenicity as compared to a control animal model.

17. The method of claim 11, wherein the method further comprises contacting or administering a PEGylated device to the animal model and monitoring the animal model for immunogenicity to the PEGylated device as compared with a control animal model.

18. The method of claim 11, wherein the method further comprises administering a PEG-containing product to the animal model and monitoring or screening the animal model for adverse reactions, wherein the PEG-containing product is selected from the group consisting of food, personal care, cosmetic, and cleaning products.

19. The method of claim 18, wherein the administering is topical or oral administration.

\* \* \* \* \*